US008124800B2

(12) United States Patent
Halperin et al.

(10) Patent No.: US 8,124,800 B2
(45) Date of Patent: Feb. 28, 2012

(54) PROCESS FOR THE PREPARATION OF OXIDIZED PHOSPHOLIPIDS

(75) Inventors: Gideon Halperin, Har-Adar (IL); Eti Kovalevski-Ishai, Netania (IL)

(73) Assignee: Vascular Biogenics Ltd., Or Yehuda (IL)

( * ) Notice: Subject to any disclaimer, the term of this patent is extended or adjusted under 35 U.S.C. 154(b) by 0 days.

(21) Appl. No.: 12/861,921

(22) Filed: Aug. 24, 2010

(65) Prior Publication Data
US 2010/0317881 A1    Dec. 16, 2010

Related U.S. Application Data

(60) Division of application No. 11/650,973, filed on Jan. 9, 2007, now Pat. No. 7,807,847, which is a continuation-in-part of application No. PCT/IL2005/000735, filed on Jul. 10, 2005.

(60) Provisional application No. 60/586,219, filed on Jul. 9, 2004.

(51) Int. Cl.
*C07F 9/02*    (2006.01)
(52) U.S. Cl. ........... 554/78; 554/150; 558/103; 560/186
(58) Field of Classification Search .................... 554/78, 554/150; 558/103; 560/186
See application file for complete search history.

(56) References Cited

U.S. PATENT DOCUMENTS
4,329,302 A    5/1982    Hanahan et al.
(Continued)

FOREIGN PATENT DOCUMENTS
CH    642665    4/1984
(Continued)

OTHER PUBLICATIONS

Communication Pursuant to Article 94(3) EPC Dated Aug. 3, 2010 From the European Patent Office Re. Application No. 05758938.4.

(Continued)

*Primary Examiner* — Deborah D Carr

(57) ABSTRACT

Novel synthetic routes, which are highly applicable for industrial preparation of therapeutically beneficial oxidized phospholipids are disclosed. Particularly, novel methods for efficiently preparing compounds having a glycerolic backbone and one or more oxidized moieties attached to the glycerolic backbone, which are devoid of column chromatography are disclosed. Further disclosed are novel methods of introducing phosphorous-containing moieties such as phosphate moieties to compounds having glycerolic backbone and intermediates formed thereby.

10 Claims, No Drawings

U.S. PATENT DOCUMENTS

| | | | |
|---|---|---|---|
| 4,614,796 | A | 9/1986 | Kawamata et al. |
| 4,778,912 | A | 10/1988 | Inoue et al. |
| 4,827,011 | A | 5/1989 | Wissner et al. |
| 4,978,670 | A | 12/1990 | Rector et al. |
| 5,561,052 | A | 10/1996 | Koike |
| 5,660,855 | A | 8/1997 | Malé-Brune |
| 5,985,292 | A | 11/1999 | Fourneron et al. |
| 6,017,513 | A | 1/2000 | Betbeder et al. |
| 6,261,597 | B1 | 7/2001 | Kurtz |
| 6,414,168 | B1 | 7/2002 | Crivello et al. |
| 6,838,452 | B2 * | 1/2005 | Harats et al. .................. 514/114 |

FOREIGN PATENT DOCUMENTS

| | | |
|---|---|---|
| WO | WO 95/23592 | 9/1995 |
| WO | WO 02/41827 | 5/2002 |
| WO | WO 2004/106486 | 12/2004 |
| WO | WO 2008/084472 | 7/2008 |

OTHER PUBLICATIONS

Examination Report Dated Oct. 27, 2010 From the Instituto Mexicano de la Propriedad Industrial Re. Application No. MX/a/2007/000361.
Office Action Dated Nov. 17, 2010 From the Israel Patent Office Re. Application No. 180628 and Its Translation Into English.
Response Dated Dec. 27, 2010 to Notice of Reason for Rejection of Oct. 19, 2010 From the Japanese Patent Office Re.: Application No. 2007-519983.
Response Dated Nov. 28, 2010 to Communication Pursuant to Article 94(3) EPC of Aug. 3, 2010 From the European Patent Office Re. Application No. 05758938.4.
Response Dated Jan. 12, 2011 to Examination Report of Oct. 27, 2010 From the Instituto Mexicano de la Propriedad Industrial Re. Application No. MX/a/2007/000361.
International Preliminary Report on Patentability Dated Sep. 15, 2008 From the International Preliminary Examining Authority Re.: Application No. PCT/IL05/00735.
Examination Report and Notice of Acceptance of Complete Specification Dated Jul. 14, 2010 From the Intellectual Property Office of New Zealand Re.: Application No. 553147.
Examination Report Dated Jul. 7, 2010 From the Intellectual Property Office of New Zealand Re. Application No. 586503.
Examination Report Dated Dec. 10, 2009 From the Intellectual Property Office of New Zealand Re.: Application No. 553147.
Examination Report Dated Apr. 21, 2009 From the Intellectual Property Office of New Zealand Re.: Application No. 553147.
International Preliminary Report on Patentability Dated Oct. 29, 2009 From the International Bureau of WIPO Re.: Application No. PCT/IL2008/000013.
International Search Report and the Written Opinion Dated Aug. 24, 2006 From the International Searching Authority Re.: Application No. PCT/IL05/00735.
International Search Report Dated Mar. 13, 2009 From the International Searching Authority Re.: Application No. PCT/IL08/00013.
Office Action Dated Nov. 13, 2009 From the State Intellectual Property Office of the People's Republic of China Re.: Application No. 200580029218.9 and Translation of Proposed Claims Into English.
Official Action Dated May 27, 2009 From the Rospatent, Federal State Office, Federal Institution of Industrial Property of the Federal Office of Intellectual Property, Patents and Trademarks of the Russian Federation Re.: Application No. 2007105097 and Its Translation Into English.
Official Action Dated Oct. 29, 2009 From the Rospatent, Federal State Office, Federal Institution of Industrial Property of the Federal Office of Intellectual Property, Patents and Trademarks of the Russian Federation Re.: Application No. 2007105097 and Its Translation Into English.
Response Dated Mar. 1, 2010 to Official Action of Dec. 1, 2009 From the US Patent and Trademark Office Re.: U.S. Appl. No. 11/650,973.
Response Dated Jan. 13, 2010 to Office Action of Nov. 13, 2009 From the State Intellectual Property Office of the People's Republic of China Re.: Application No. 200580029218.9.

Response Dated May 17, 2010 to Examination Report of Dec. 10, 2009 From the Intellectual Property Office of New Zealand Re.: Application No. 553147.
Response Dated Jan. 28, 2010 to Official Action of Oct. 29, 2009 From the Rospatent, Federal State Office, Federal Institution of Industrial Property of the Federal Office of Intellectual Property, Patents and Trademarks of the Russian Federation Re.: Application No. 2007105097.
Revised Response Dated Jun. 20, 2010 to Examination Report of Dec. 10, 2009 From the Intellectual Property Office of New Zealand Re.: Application No. 553147.
Supplementary Partial European Search Report and the European Search Opinion Dated Nov. 30, 2009 From the European Patent Office Re.: Application No. 05758938.4.
Translation of Notice of Reason for Rejection Dated Feb. 26, 2010 From the Japanese Patent Office Re.: Application No. 2007-519983.
Translation of Office Action Dated May 8, 2009 From the State Intellectual Property Office of the Peopl's Republic of China Re.: Application No. 200580029218.9.
Written Opinion Dated Mar. 13, 2009 From the International Searching Authority Re.: Application No. PCT/IL08/00013.
Boullier et al. "The Binding of Oxidized Low Density Lipoprotein to Mouse CD36 Is Mediated in Part by Oxidized Phospholipids That Are Associated With Both the Lipid and Protein Moieties of the Lipoprotein",Jornal of Biological Chemistry, vol. 275 (13) p. 9163-9169, 2000.
Davies et al. "Oxidized Alkyl Phospholipids Are Specific, High Affinity Peroxisome Proliferator- Activated Receptor γ ligands and Agonists", Jornal of Biological Chemistry, vol. 26 (19), p. 16015-16023, 2001.
George et al. "Hyperimmunization of Apo-E-Deficient Mice Homologous Malondialdehyde Low-Density Lipoprotein Suppresses early Atherogenesis", Atherosclerosis 138, p. 147-152, 1998.
Itabe et al. "Oxidized Phosphatidylcholines That Modify Proteins", Jornal of Biological Chemistry, vol. 271 (52), p. 33208-33217, 1996.
Leitinger et al. "Structurally Similar Oxidized Phospholipids Differentially Regulate Endothelial Binding of Monocytes and Neutrophils", Proc. Natl. Acad. Sci. USA, 96(21): 12010-12015, 1999.
Subbanagounder et al. "Determinants of Bioactivity of Oxydized Phospholipids: Specific Oxidized Fatty Acyl Groups at the SN-2 Position," Arteriosclerosis Thromb. Vasc. Biol., p. 2248-2254, 2000.
Subbanagounder et al. "Evidence That Phospholipid Oxidation Products and/or Platelet-Activating Factor Play an Important Role in Early Atherogenesis: In Vitro and In Vivo Inhibition by Web 2086", Circulation Research, 85: 311-318, 1999.
Tokumura et al. "Cardiovascular Effects of Lysophophatidic Acid and Its Structural Analogs in Rats", The Journal of Pharmacology and Experimental Therapeutics, 219(1): 219-222, 1981.
Watson et al. "Structural Identification by Mass Spectrometry of Oxidized Phospholipids in Minimally Oxidized Low Density Lipoprotein That Induce Monocyte/Endothelial Interactions and Evidence for Their Presence in Vivo".
Invitation Pursuant to Rule 62a(1) EPC Dated Jul. 8, 2010 From the European Patent Office Re. Application No. 08700247.3.
Response Dated Sep. 7, 2010 to Invitation Pursuant to Rule 62a(1) EPC of Jul. 8, 2010 From the European Patent Office Re. Application No. 08700247.3.
Examiner's Report Dated Aug. 31, 2010 From the Australian Government, IP Australia Re. Application No. 2007200090.
Translation of Notice of Reason for Rejection Dated Oct. 19, 2010 From the Japanese Patent Office Re.: Application No. 2007-519983.
Response Dated Oct. 2, 2011 to Examination Report of Jul. 29, 2011 From the Instituto Mexicano de la Propriedad Industrial Re. Application No. MX/a/2009/007422.
Communication Pursuant to Article 94(3) EPC Dated Jun. 30, 2011 From the European Patent Office Re. Application No. 05758938.4.
Examination Report Dated Jul. 22, 2011 From the Intellectual Property Office of New Zealand Re. Application No. 593529.
Examination Report Dated Jun. 23, 2011 From the Intellectual Property Office of New Zealand Re. Application No. 578947.

Examination Report Dated Jul. 29, 2011 From the Instituto Mexicano de la Propriedad Industrial Re. Application No. MX/a/2009/007422 and Its Translation Into English.

Response Dated Aug. 9, 2011 to Examination Report of Jun. 23, 2011 From the Intellectual Property Office of New Zealand Re. Application No. 578947.

Response Dated Mar. 17, 2011 to Office Action of Nov. 17, 2010 From the Israel Patent Office Re. Application No. 180628.

Notification to Grant Patent Right for Invention Dated Apr. 6, 2011 From the State Intellectual Property Office of the Peopl's Republic of China Re.: Application No. 200580029218.9 and Its Translation Into English.

Response Dated Feb. 1, 2011 to Examination Report of Jul. 7, 2010 From the Intellectual Property Office of New Zealand Re. Application No. 586503.

"The Nomenclature of Lipids", Journal of Lipid Research, vol. 8: 523-528,1967. e-mail pdf of Jul. 29, 2011 (Filing) in 46755.

Examination Report Dated Sep. 16, 2010 From the Intellectual Property Office of New Zealand Re. Application No. 578947.

Response Dated May 26, 2011 to Examination Report of Sep. 16, 2010 From the Intellectual Property Office of New Zealand Re. Application No. 578947.

Office Action Dated Jul. 21, 2011 From the Israeli Patent Office Re. Application No. 211795 and Its Translation Into English.

Response Dated Aug. 10, 2011 to Communication Pursuant to Article 94(3) EPC of Jun. 30, 2011 From the European Patent Office Re. Application No. 05758938.4.

Response Dated Aug. 11, 2011 to Communication Pursuant to Article 94(3) EPC of Apr. 14, 2011 From the European Patent Office Re. Application No. 08700247.3.

Response Dated Aug. 16, 2011 to Examiner's Report of Aug. 31, 2010 From the Australian Government, IP Australia Re. Application No. 2007200090.

Examination Report Dated Jun. 22, 2011 From the Intellectual Property Office of New Zealand Re. Application No. 593529.

Communication Pursuant to Article 94(3) EPC Dated Apr. 14, 2011 From the European Patent Office Re. Application No. 08700247.3.

Supplementary Partial European Search Report Dated Apr. 4, 2011 From the European Patent Office Re. Application No. 08700247.3.

Translation of Office Action Dated Sep. 5, 2011 From the State Intellectual Property Office of the People's Republic of China Re. Application No. 201010128184.1.

* cited by examiner

PROCESS FOR THE PREPARATION OF OXIDIZED PHOSPHOLIPIDS

RELATED APPLICATIONS

This is application is a divisional of U.S. patent application Ser. No. 11/650,973, filed on Jan. 9, 2007, which is a continuation-in-part of International Patent Application No. PCT/IL2005/000735 (WO2006/006161), filed on Jul. 10, 2005, which claims the benefit of priority from U.S. Provisional Patent Application No. 60/586,219, filed on Jul. 9, 2004, the teachings of both being incorporated herein in their entirety.

FIELD AND BACKGROUND OF THE INVENTION

The present invention relates to the field of synthetic chemistry, and more particularly, to novel synthetic processes useful for the preparation of oxidized phospholipids, derivatives, analogs and salts thereof.

In the art of pharmacology, modified phospholipids are known in many applications. In U.S. Pat. No. 5,985,292 compositions for trans-dermal and trans-membranal application incorporating phospholipids bearing lipid-soluble active compounds are disclosed. In U.S. Pat. Nos. 6,261,597, 6,017,513 and 4,614,796 phospholipid derivatives incorporated into liposomes and biovectors for drug delivery are disclosed. In U.S. Pat. No. 5,660,855 lipid constructs of aminomannose-derivatized cholesterol suitable for targeting smooth muscle cells or tissue, formulated in liposomes, are disclosed. These formulations are aimed at reducing restenosis in arteries, using PTCA procedures.

The use of liposomes for treating atherosclerosis has been further disclosed in the PCT patent application published as WO 95/23592. Therein are disclosed pharmaceutical compositions of unilamellar liposomes that may contain phospholipids. The liposomes disclosed in WO 95/23592 are aimed at optimizing cholesterol efflux from atherosclerotic plaque and are typically non-oxidized phospholipids.

Modified phospholipid derivatives mimicking platelet activation factor (PAF) structures are known to be pharmaceutically active, affecting such functions as vascular permeability, blood pressure and heart function inhibition. In U.S. Pat. No. 4,778,912 it is suggested that one group of such derivatives has anti-cancer activity.

In U.S. Pat. No. 4,329,302 synthetic 1-O-alkyl ether or 1-O-fatty acyl phosphoglycerides compounds which are lysolechitin derivatives usable in mediating platelet activation are disclosed. In U.S. Pat. No. 4,329,302 is disclosed that small chain acylation of lysolechitin gave rise to compounds with platelet activating behavior, as opposed to long-chain acylation, and that the 1-O-alkyl ether are biologically superior to the corresponding 1-O-fatty acyl derivatives in mimicking PAF.

The structural effect of various phospholipids on the biological activity thereof has been investigated by Tokumura et al. (Journal of Pharmacology and Experimental Therapeutics. July 1981, Vol. 219, No. 1) and in U.S. Pat. No. 4,827,011, with respect to hypertension.

In Swiss patent CH 642,665 modified phospholipid ether derivatives that may have some physiological effect are disclosed.

Davies et al. (J. Biol. Chem. 2001, 276:16015) teach the use of oxidized phospholipids as peroxisome proliferator-activated receptor agonists.

In U.S. Pat. No. 6,838,452 and in WO 04/106486 (which are incorporated by reference as if fully set forth herein), by the present assignee, the preparation of well-defined oxidized phospholipids, as well as other synthetic oxidized LDL (low density lipoprotein) components, is disclosed. The disclosed compounds are reported to be highly effective in treating atherosclerosis and related diseases, as well as autoimmune diseases and inflammatory disorders. It is further reported that the oxidized phospholipid regulate the immune response to oxidized LDL. It is further reported that generally, etherified oxidized phospholipids are superior to comparable esterified oxidized phospholipids as therapeutic agents.

Oxidation of phospholipids occurs in vivo through the action of free radicals and enzymatic reactions abundant in atheromatous plaque. In vitro, preparation of oxidized phospholipids usually involves simple chemical oxidation of a native LDL or LDL phospholipid component. Investigators studying the role of oxidized LDL have employed, for example, ferrous ions and ascorbic acid (Itabe, H., et al., J. Biol. Chem. 1996; 271:33208-217) and copper sulfate (George, J. et al., Atherosclerosis. 1998; 138:147-152; Ameli, S. et al., Arteriosclerosis Thromb Vasc Biol 1996; 16:1074-79) to produce oxidized, or mildly oxidized phospholipid molecules similar to those associated with plaque components. Similarly prepared molecules have been shown to be identical to auto-antigens associated with atherogenesis (Watson A. D. et al., J. Biol. Chem. 1997; 272:13597-607) and able to induce protective anti-atherogenic immune tolerance (U.S. patent application Ser. No. 09/806,400 to Shoenfeld et al., filed Sep. 30, 1999) in mice. Similarly, in U.S. Pat. No. 5,561,052, a method of producing oxidized lipids and phospholipids using copper sulfate and superoxide dismutase to produce oxidized arachidonic or linoleic acids and oxidized LDL for diagnostic use is disclosed.

The oxidation techniques described above for preparing oxidized phospholipids involve reactions that are non-specific and yield a mixture of oxidized products. The non-specificity of the reactions reduces yield, requires a further separation step and raises concern for undesired side effects when the products are integrated in pharmaceutical compositions.

1-Palmitoyl-2-(5-oxovaleroyl)-sn-glycero-3-phosphocholine (POVPC) and derivatives thereof such as 1-palmitoyl-2-glutaroyl-sn-glycero-3-phosphocholine GPC) are representative examples of mildly oxidized esterified phospholipids that have been studied with respect to atherogenesis (see, for example, Boullier et al., J. Biol. Chem. 2000, 275:9163; Subbanagounder et al., Circulation Research, 1999, pp. 311). The effect of different structural analogs that belong to this class of oxidized phospholipids has also been studied (see, for example, Subbanagounder et al., Arterioscler. Thromb. Nasc. Biol. 2000, pp. 2248; Leitinger et al., Proc. Nat. Ac. Sci. 1999, 96:12010).

POVPC is typically prepared by providing a phosphatidyl choline bearing an unsaturated fatty acid and oxidizing the unsaturated bond of the fatty acid by, e.g., ozonolysis (oxidative cleavage) or using a periodate as an oxidizing agent. Such a synthetic pathway typically involves a multi-step synthesis and requires separation of most of the formed intermediates by means of column chromatography.

As described in U.S. Pat. No. 6,838,452 cited above, etherified oxidized phospholipids have been similarly prepared by oxidizing an unsaturated bond of a fatty acid attached to a phospholipid backbone. More particularly, the etherified oxidized phospholipids were prepared, according to the teachings of this patent, by introducing an unsaturated short fatty acid to a glycerolipid, introducing a phosphate moiety to the obtained intermediate and oxidizing the unsaturated bond in the fatty acid chain by means of (i) hydrogen peroxide and formic acid, so as to obtain a diol, followed by potassium periodate, so as to obtain an aldehyde; or (ii) ozonolysis. While the oxidative cleavage of the unsaturated bond results in an aldehyde moiety, other oxidized moieties (e.g., carboxylic acid, acetal, etc.) were obtained by further oxidizing the aldehyde moiety. Such a multi-step synthetic pathway is oftentimes characterized by relatively low overall yields and again, requires separation of most of the formed intermediates by means of column chromatography.

It has been found that in vivo applications employing esterified oxidized phospholipids prepared as above have the disadvantage of susceptibility to recognition, binding and metabolism of the active component in the body, making dosage and stability after administration an important consideration. Etherified oxidized phospholipids, such as those described in U.S. Pat. No. 6,838,452 and in WO 04/106486, exhibit higher biostability and high therapeutic activity.

Thus, the currently known methods of preparing etherified, as well as esterified, oxidized phospholipids involve complex multi-step procedures suitable for laboratory preparation yet rendering industrial scale preparation inefficient and complex. In particular, these multi-step procedures require industrially inapplicable separation techniques such as column chromatography during various stages of the synthetic process.

In view of the beneficial therapeutic activity of oxidized phospholipids in general and of etherified oxidized phospholipids in particular, there is a widely recognized need for and it would be highly advantageous to have an improved process for the preparation of etherified oxidized phospholipids devoid of at least some of the disadvantages of processes known in the art.

SUMMARY OF THE INVENTION

According to one aspect of the present invention there is provided a method of preparing a compound having a glycerolic backbone and at least one oxidized moiety-containing residue attached to the glycerolic backbone via an ether bond, which comprises: providing a first compound having a glycerolic backbone and at least one free hydroxyl group; providing a second compound having at least one unsaturated bond and at least one reactive group capable of forming an ether bond with the free hydroxyl group; reacting the first compound and the second compound to thereby obtain a third compound, the third compound having a glycerolic backbone and an unsaturated bond-containing residue being attached to the glycerolic backbone via an ether bond; isolating the third compound, to thereby obtain a purified third compound; reacting the purified third compound with an oxidizing agent, to thereby obtain a fourth compound, the fourth compound having a glycerolic backbone and an oxidized moiety-containing residue attached to the glycerolic backbone via an ether bond; and isolating the fourth compound to thereby obtain a purified fourth compound, thereby obtaining the compound having a glycerolic backbone and at least one oxidized moiety-containing residue attached to the glycerolic backbone via an ether bond, the method being devoid of column chromatography.

According to further features in preferred embodiments of the invention described below, reacting the first compound and the second compound is carried out in the presence of a base.

According to still further features in the described preferred embodiments the base is selected from the group consisting of sodium hydroxide, lithium hydroxide, calcium hydroxide, barium hydroxide and potassium hydroxide.

According to still further features in the described preferred embodiments the reactive group is a halide.

According to still further features in the described preferred embodiments isolating the third compound comprises: collecting the third compound; providing a solution of the third compound in a solvent, the solvent being selected such that the third compound is soluble therein whereby impurities formed during the reacting are insoluble therein, to thereby provide a mixture including the solution of the third compound in the solvent and insoluble impurities; removing the insoluble impurities; and removing the solvent, thereby obtaining the purified third compound.

According to still further features in the described preferred embodiments the solvent is selected from the group consisting of petrol ether, hexane and benzene.

According to still further features in the described preferred embodiments the oxidizing agent is selected from the group consisting of formic acid, hydrogen peroxide, a periodate, a perchlorate, a bismuthate, a permanganate, a chlorite, ozone, silver oxide, osmium tetraoxide and any combination thereof.

According to still further features in the described preferred embodiments the oxidized moiety is selected from the group consisting of a carboxylic acid, an ester, an aldehyde, an acetal, a ketal and a diol.

According to still further features in the described preferred embodiments the oxidized moiety is aldehyde and reacting the purified third compound with the oxidizing agent comprises: converting the purified third compound to a compound having a glycerolic backbone and a diol-containing residue attached to the glycerolic backbone via an ether bond; and oxidizing the compound having a glycerolic backbone and a diol-containing residue attached to the glycerolic backbone, to thereby obtain the fourth compound having a glycerolic backbone and an aldehyde-containing residue attached to the glycerolic backbone via an ether bond.

According to still further features in the described preferred embodiments the converting is effected by reacting the purified third compound with a first oxidizing agent selected from the group consisting of a peroxide, a bismuthate, a periodate, a permanganate, and any combination thereof.

According to still further features in the described preferred embodiments the oxidizing is effected by reacting the compound having a glycerolic backbone and a diol-containing residue attached to the glycerolic backbone with a second oxidizing agent selected from the group consisting of a periodate, a bismuthate, a permanganate, and a chlorite According to still further features in the described preferred embodiments isolating the fourth compound comprises: collecting the fourth compound; providing a water-soluble adduct of the fourth compound; subjecting the water-soluble adduct to a biphasic system, to thereby provide an aqueous phase containing the adduct and an organic phase containing water-insoluble impurities formed during the reacting with the oxidizing agent; collecting the aqueous phase; decomposing the adduct; and collecting the fourth compound, thereby obtaining the purified fourth compound.

According to still further features in the described preferred embodiments providing the water-soluble adduct comprises: reacting the fourth compound with a Girard reagent.

According to still further features in the described preferred embodiments the oxidized moiety is a carboxylic acid and reacting the purified third compound with the oxidizing agent comprises: converting the purified third compound to a compound having a glycerolic backbone and an aldehyde-containing residue attached to the glycerolic backbone via an ether bond; and oxidizing the compound having a glycerolic backbone and an aldehyde-containing residue attached to the glycerolic backbone, to thereby obtain a compound having a glycerolic backbone and a carboxylic acid-containing residue attached to the glycerolic backbone via an ether bond.

According to still further features in the described preferred embodiments converting the purified third compound to the compound having a glycerolic backbone and an aldehyde-containing residue attached to the glycerolic backbone via an ether bond comprises: converting the purified third compound to a compound having a glycerolic backbone and a diol-containing residue attached to the glycerolic backbone via an ether bond; and oxidizing the compound having a glycerolic backbone and a diol-containing residue attached to the glycerolic backbone, to thereby obtain the compound having a glycerolic backbone and an aldehyde-containing residue attached to the glycerolic backbone via an ether bond.

According to still further features in the described preferred embodiments the method further comprises isolating the compound having a glycerolic backbone and an aldehyde-containing residue attached to the glycerolic backbone via an ether bond, to thereby obtain a purified compound having a glycerolic backbone and an aldehyde-containing residue attached to the glycerolic backbone via an ether bond.

According to still further features in the described preferred embodiments the isolating comprises: collecting the compound having a glycerolic backbone and an aldehyde-containing residue attached to the glycerolic backbone via an ether bond; providing a water-soluble adduct of the compound having a glycerolic backbone and an aldehyde-containing residue attached to the glycerolic backbone via an ether bond, as described hereinabove; subjecting the water-soluble adduct to a biphasic system, to thereby provide an aqueous phase containing the complex and an organic phase containing water-insoluble impurities formed during the converting and/or the oxidizing; collecting the aqueous phase; decomposing the adduct; and collecting the compound having a glycerolic backbone and an aldehyde-containing residue attached to the glycerolic backbone via an ether bond, thereby obtaining a purified compound having a glycerolic backbone and an aldehyde-containing residue attached to the glycerolic backbone via an ether bond.

According to still further features in the described preferred embodiments the oxidized moiety is a carboxylic acid and reacting the purified third compound with the oxidizing agent comprises: converting the purified third compound to a compound having a glycerolic backbone and an epoxide-containing residue attached to the glycerolic backbone via an ether bond; and oxidizing the compound having a glycerolic backbone and an epoxide-containing residue attached to the glycerolic backbone, to thereby obtain a compound having a glycerolic backbone and a carboxylic acid-containing residue attached to the glycerolic backbone via an ether bond.

According to still further features in the described preferred embodiments the converting comprises reacting the third compound with a peroxide.

According to still further features in the described preferred embodiments the oxidized moiety is a carboxylic acid and reacting the purified third compound with the oxidizing agent comprises reacting the purified third compound with a mixture of a permanganate and a periodate.

According to still further features in the described preferred embodiments the said reacting is effected in the presence of a base.

According to still further features in the described preferred embodiments the first compound has at least two free hydroxyl groups, the method further comprising, prior to the reacting the first compound and the second compound: protecting at least one of the at least two groups with a protecting group.

According to still further features in the described preferred embodiments the protecting group is trityl.

According to still further features in the described preferred embodiments the first compound has at least two free hydroxyl groups, the method further comprising, prior to the reacting the first compound and the second compound: protecting at least one of the at least two groups with a protecting group, preferably a trityl group.

According to still further features in the described preferred embodiments, when the methods include the formation of an epoxide-containing compound, as described hereinabove, the method further comprises, prior to reacting the third compound and the oxidizing agent: replacing the trityl with a protecting group selected from the group consisting of acetate, pivaloate or benzoate.

According to still further features in the described preferred embodiments the compound having a glycerolic backbone and at least one oxidized moiety-containing residue attached to the glycerolic backbone further comprises a phosphorous-containing moiety attached to the glycerolic backbone, and the method further comprises, prior to reacting the first compound and the second compound, prior to isolating the third compound, prior to reacting the third compound with the oxidizing agent, prior to isolating the fourth compound or subsequent to isolating the fourth compound:

reacting the first compound, the third compound, the purified third compound, the fourth compound or the purified fourth compound with a phosphorous-containing moiety, to thereby obtain the compound having a glycerolic backbone and at least one oxidized moiety-containing residue attached to the glycerolic backbone and further having a phosphorous-containing moiety attached to the glycerolic backbone.

According to still further features in the described preferred embodiments the at least one phosphorous-containing moiety is a phosphate moiety being attached to the glycerolic backbone via a phosphodiester bond.

According to still further features in the described preferred embodiments the at least one phosphorous-containing moiety is selected from the group consisting of phosphoric acid, phosphoryl choline, phosphoryl ethanolamine, phosphoryl serine, phosphoryl cardiolipin, phosphoryl inositol, ethylphosphocholine, phosphorylmethanol, phosphorylethanol, phosphorylpropanol, phosphorylbutanol, phosphorylethanolamine-N-lactose, phosphoethanolamine-N-[methoxy (propylene glycol)], phosphoinositol-4-phosphate, phosphoinositol-4,5-biposphonate, pyrophosphate, phosphoethanolamine-diethylenetriamine-pentaacetate, dinitrophenyl-phosphoethanolamine and phosphoglycerol.

According to still further features in the described preferred embodiments the phosphorous-containing moiety is attached to the sn-3 position of the glycerolic backbone of the compound.

According to still further features in the described preferred embodiments reacting the first compound, the third compound, the purified third compound, the fourth compound or the purified fourth compound with the phosphorous-containing moiety comprises: providing the first compound, the third compound, the purified third compound, the fourth compound or the purified fourth compound having a free hydroxyl group; reacting the first compound, the third compound, the purified third compound, the fourth compound or the purified fourth compound with a reactive phosphorous-containing compound having a second reactive group and a third reactive group, the second reactive group being capable of reacting with the free hydroxyl group and a second reactive group, to thereby provide the first compound, the third compound, the purified third compound, the fourth compound or the purified fourth compound having a reactive phosphorous-containing group attached to the glycerolic backbone; and converting the reactive phosphorous-containing group to the phosphorous-containing moiety.

According to still further features in the described preferred embodiments the reactive phosphorous-containing compound is phosphorous oxychloride ($POCl_3$).

According to still further features in the described preferred embodiments the reacting is carried out in the presence of a base.

According to still further features in the described preferred embodiments the phosphorous-containing moiety is phosphoric acid, and the converting comprises hydrolyzing the reactive phosophrous-containing group.

According to still further features in the described preferred embodiments the phosphorous-containing moiety comprises an aminoalkyl group and the converting comprises reacting the reactive phosophrous-containing group with a derivative of the aminoalkyl group, the derivative being selected capable of reacting with the third reactive group.

According to another aspect of the present invention there is provided another method of preparing a compound having a glycerolic backbone and at least one oxidized moiety-containing residue attached to the glycerolic backbone via an ether bond, the method comprising: providing a first compound having a glycerolic backbone and at least one free hydroxyl group; providing a fifth compound having at least one oxidized moiety and at least one fourth reactive group; reacting the first compound and the fifth compound to thereby obtain a reaction mixture containing a sixth compound, the sixth compound being the compound having a glycerolic backbone and at least one oxidized moiety-containing residue attached to the glycerolic backbone via an ether bond; and isolating the compound having a glycerolic backbone and at least one oxidized moiety-containing residue attached to the glycerolic backbone via an ether bond.

According to further features in preferred embodiments of the invention described below, reacting the first compound and the fifth compound is effected in the presence of a base.

According to still further features in the described preferred embodiments the base is selected from the group consisting of sodium hydride, lithium aluminum hydride, sodium amide, sodium hydroxide, potassium hydroxide and any mixture thereof.

According to still further features in the described preferred embodiments the fourth reactive group is a halide.

According to still further features in the described preferred embodiments the oxidized moiety is selected from the group consisting of a carboxylic acid, an ester, an acyl halide, an aldehyde, an acetal, a ketal and a diol According to still further features in the described preferred embodiments the fifth compound comprises less than 4 carbon atoms.

According to still further features in the described preferred embodiments the fifth compound comprises more than 5 carbon atoms.

According to still further features in the described preferred embodiments the first compound has at least two free hydroxyl groups, the method further comprising, prior to the reacting the first compound and the fifth compound: protecting at least one of the at least two groups with a protecting group.

According to still further features in the described preferred embodiments the protecting group is trityl.

According to still further features in the described preferred embodiments the compound having a glycerolic backbone and at least one oxidized moiety-containing residue attached to the glycerolic backbone further comprises a phosphorous-containing moiety attached to the glycerolic backbone, the method further comprising, prior to or subsequent to reacting the first compound and the fifth compound, or subsequent to isolating the sixth compound: reacting the first compound or the sixth compound with a phosphorous-containing moiety, to thereby obtain the compound having a glycerolic backbone and at least one oxidized moiety-containing residue attached to the glycerolic backbone and further having a phosphorous-containing moiety attached to the glycerolic backbone, as described hereinabove.

According to further features in preferred embodiments of the invention described below, in any of the methods described herein, the first compound further comprises at least one alkylene chain having 1-30 carbon atoms.

According to still further features in the described preferred embodiments the alkylene chain is attached to the glycerolic backbone via an ether bond.

According to still further features in the described preferred embodiments the alkylene chain is attached to the sn-1 position of the glycerolic backbone of the first compound.

According to still further features in the described preferred embodiment the oxidized moiety-containing residue is attached to the sn-2 position of the compound and further wherein at least one of the free hydroxyl groups of the glycerolic backbone is at the sn-2 position of the first compound.

According to still further features in the described preferred embodiments the first compound has the general formula I:

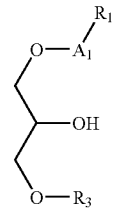

Formula I wherein:

$A_1$ is absent or is selected from the group consisting of $CH_2$, $CH=CH$ and $C=O$;

$R_1$ is selected from the group consisting of H and a hydrocarbon chain having from 1 to 30 carbon atoms; and $R_3$ is selected from the group consisting of hydrogen, alkyl, aryl, phosphoric acid, phosphoryl choline, phosphoryl ethanolamine, phosphoryl serine, phosphatidyl choline, phosphatidyl ethanolamine, phosphatidyl serine, phosphatidyl cardiolipin, phosphatidyl inositol, phosphoryl cardiolipin, phosphoryl inositol, ethylphosphocholine, phosphorylmethanol, phosphorylethanol, phosphorylpropanol, phosphorylbutanol, phosphorylethanolamine-N-lactose, phosphoethanolamine-N-[methoxy(propylene glycol)], phosphoinositol-4-phosphate, phosphoinositol-4,5-bisphosphonate, pyrophosphate, phosphoethanolamine-diethylenetriamine-pentaacetate, dinitrophenyl-phosphoethanolamine, phosphoglycerol.

According to still further features in the described preferred embodiments the compound having a glycerolic compound and at least one oxidized moiety attached to the glycerolic backbone via an ether bond has the general Formula II:

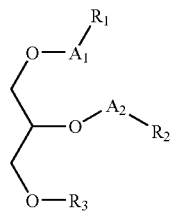

Formula II wherein:

$A_1$ is selected from the group consisting of $CH_2$, $CH=CH$ and $C=O$;

$A_2$ is $CH_2$;

$R_1$ is an alkyl having 1-30 carbon atoms;

$R_2$ is

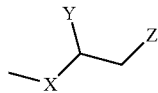

whereas:

X is an alkyl chain having 1-24 carbon atoms;

Y is selected from the group consisting of hydrogen, hydroxy, alkyl, alkoxy, halide, acetoxy and an aromatic functional group; and Z is selected from the group consisting of:

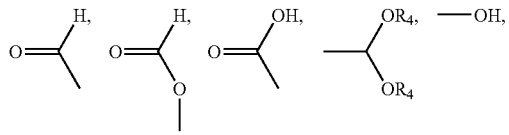

with $R_4$ being an alkyl or aryl; and $R_3$ is selected from the group consisting of hydrogen, alkyl, aryl, phosphoric acid, phosphoryl choline, phosphoryl ethanolamine, phosphoryl serine, phosphatidyl choline, phosphatidyl ethanolamine, phosphatidyl serine, phosphatidyl cardiolipin, phosphatidyl inositol, phosphoryl cardiolipin, phosphoryl inositol, ethylphosphocholine, phosphorylmethanol, phosphorylethanol, phosphorylpropanol, phosphorylbutanol, phosphorylethanolamine-N-lactose, phosphoethanolamine-N-[methoxy(propylene glycol)], phosphoinositol-4-phosphate, phosphoinositol-4,5-biposphonate, pyrophosphate, phosphoethanolamine-diethylenetriamine-pentaacetate, dinitrophenyl-phosphoethanolamine, phosphoglycerol.

According to still another aspect of the present invention there is provided a method of introducing a phosphate moiety into a compound having a glycerolic backbone and having an oxidized moiety-containing or a pre-oxidized moiety-containing residue attached thereto via an ether bond, which comprises: providing a compound having a glycerolic backbone and an oxidized moiety- or a pre-oxidized moiety-containing residue attached to the glycerolic backbone via an ether bond and at least one a free hydroxyl group; reacting the compound a phosphorous-containing compound having a second reactive group and a third reactive, the second reactive group being capable of reacting with the free hydroxyl group, to thereby provide a compound having an oxidized moiety- or a pre-oxidized moiety-containing residue and a reactive phosphorous-containing group; and converting the reactive phosphorous-containing group to the phosphate moiety, thereby introducing the phosphate moiety into the compound.

According to further features in preferred embodiments of the invention described below, the compound having the glycerolic backbone comprises at least one alkylene chain having 1-30 carbon atoms.

According to still further features in the described preferred embodiments the alkylene chain is attached to the glycerolic backbone via an ether bond.

According to still further features in the described preferred embodiments the alkylene chain is attached to the sn-1 position of the glycerolic backbone of the compound.

According to still further features in the described preferred embodiments the oxidized moiety is selected from the group consisting of carboxylic acid, ester, acyl halide, aldehyde, acetal, diol and ketal.

According to still further features in the described preferred embodiments the pre-oxidized moiety is an unsaturated moiety.

According to still further features in the described preferred embodiments the phosphorous-containing compound is $POCl_3$.

According to still further features in the described preferred embodiments the reacting is performed in the presence of a base.

According to still further features in the described preferred embodiments the base is a tertiary amine.

According to still further features in the described preferred embodiments the phosphorous-containing compound is $POCl_3$, and the reactive phosphorous-containing group is a dichlorophosphate group.

According to still further features in the described preferred embodiments the compound having the glycerolic backbone has a pre-oxidized moiety-containing residue attached thereto via an ether bond.

According to still further features in the described preferred embodiments the phosphate moiety is selected from the group consisting of phosphoric acid, phosphoryl choline, phosphoryl ethanolamine, phosphoryl serine, phosphoryl cardiolipin, phosphoryl inositol, phosphoryl cardiolipin, ethylphosphocholine, phosphorylmethanol, phosphorylethanol, phosphorylpropanol, phosphorylbutanol, phosphorylethanolamine-N-lactose, phosphoethanolamine-N-[methoxy(propylene glycol)], phosphoinositol-4-phosphate, phosphoinositol-4,5-biposphonate, pyrophosphate, phosphoethanolamine-diethylenetriamine-pentaacetate, dinitrophenyl-phosphoethanolamine, phosphoglycerol.

According to still further features in the described preferred embodiments the phosphate moiety is phosphoric acid and the converting comprises hydrolyzing the reactive phosphorous-containing group.

According to still further features in the described preferred embodiments the phosphate moiety comprises an alkylamino group and the converting comprises reacting the reactive phosphorous-containing moiety with a derivative of an aminoalkyl, the derivative being capable of reacting with the reactive phosphorous-containing group.

According to still another aspect of the present invention there is provided a method of preparing a compound having a glycerolic compound and at least one oxidized moiety attached to the glycerolic backbone via an ether bond, the compound having the general Formula II:

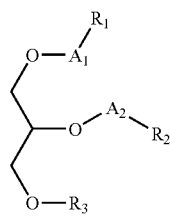

Formula II wherein: $A_1$ is selected from the group consisting of $CH_2$, CH=CH and C=O; $A_2$ is $CH_2$; $R_1$ is an alkyl having 1-30 carbon atoms; $R_2$ is

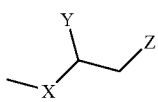

whereas: X is an alkyl chain having 1-24 carbon atoms; Y is selected from the group consisting of hydrogen, hydroxy, alkyl, alkoxy, halide, acetoxy and an aromatic functional group; and Z is selected from the group consisting of:

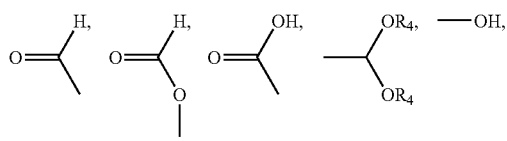

with $R_4$ being an alkyl or aryl; and $R_3$ is selected from the group consisting of hydrogen, alkyl, aryl, phosphoric acid, phosphoryl choline, phosphoryl ethanolamine, phosphoryl serine, phosphatidyl choline, phosphatidyl ethanolamine, phosphatidyl serine, phosphatidyl cardiolipin, phosphatidyl inositol, phosphoryl cardiolipin, phosphoryl inositol, ethylphosphocholine, phosphorylmethanol, phosphorylethanol, phosphorylpropanol, phosphorylbutanol, phosphorylethanolamine-N-lactose, phosphoethanolamine-N4-[methoxy(propylene glycol)], phosphoinositol-4-phosphate, phosphoinositol-4,5-biposphonate, pyrophosphate, phosphoethanolamine-diethylenetriamine-pentaacetate, dinitrophenyl-phosphoethanolamine, phosphoglycerol, the method comprising:

providing a first compound having a glycerolic backbone and at least one free hydroxyl group, the first compound having general Formula I:

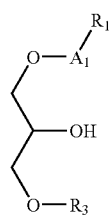

Formula I providing a second compound having at least one unsaturated bond and at least one reactive group capable of forming an ether bond with the free hydroxyl group; reacting the first compound and the second compound to thereby obtain a third compound, the third compound having the glycerolic backbone and an unsaturated bond-containing residue being attached to the glycerolic backbone via an ether bond at position sn-2; isolating the third compound, to thereby obtain a purified third compound; reacting the purified third compound with an oxidizing agent, to thereby obtain a fourth compound, the fourth compound having the glycerolic backbone and an oxidized moiety-containing residue attached to the glycerolic backbone via an ether bond at position sn-2; and isolating the fourth compound to thereby obtain a purified fourth compound, thereby obtaining the compound having a glycerolic backbone and at least one oxidized moiety-containing residue attached to the glycerolic backbone via an ether bond, the method being devoid of column chromatography.

According to further features in preferred embodiments of the invention described below, isolating the third compound comprises: collecting the third compound; providing a solution of the third compound in a solvent, the solvent being selected such that the third compound is soluble therein whereby impurities formed during the reacting are insoluble therein, to thereby provide a mixture including the solution of the third compound in the solvent and insoluble impurities; removing the insoluble impurities; and removing the solvent, thereby obtaining the purified third compound.

According to still further features in the described preferred embodiments the oxidized moiety is selected from the group consisting of a carboxylic acid and an ester.

According to still further features in the described preferred embodiments the oxidizing agent comprises a mixture of a periodate and a permanganate.

According to still further features in the described preferred embodiments reacting the purified third compound with an oxidizing agent is effected in the presence of a base.

According to still further features in the described preferred embodiments wherein $R_3$ is hydrogen, the method further comprising, prior to the reacting the first compound and the second compound: protecting a free hydroxyl group at position sn-3 of the glycerolic backbone with a protecting group.

According to still further features in the described preferred embodiments the compound having a glycerolic backbone and at least one oxidized moiety-containing residue attached to the glycerolic backbone further comprises a phosphorous-containing moiety attached to the glycerolic backbone, such that $R_3$ is selected from the group consisting of phosphoric acid, phosphoryl choline, phosphoryl ethanolamine, phosphoryl serine, phosphatidyl choline, phosphatidyl ethanolamine, phosphatidyl serine, phosphatidyl cardiolipin, phosphatidyl inositol, phosphoryl cardiolipin, phosphoryl inositol, ethylphosphocholine, phosphorylmethanol, phosphorylethanol, phosphorylpropanol, phosphorylbutanol, phosphorylethanolamine-N-lactose, phosphoethanolamine-N-[methoxy(propylene glycol)], phosphoinositol-4-phosphate, phosphoinositol-4,5-biposphonate, pyrophosphate, phosphoethanolamine-diethylenetriamine-pentaacetate, dinitrophenyl-phosphoethanolamine, phosphoglycerol, the method further comprising, subsequent to isolating the fourth compound: reacting the purified fourth compound with a phosphorous-containing moiety, to thereby obtain the compound having a glycerolic backbone and at least one oxidized moiety-containing residue attached to the glycerolic backbone and further having a phosphorous-containing moiety attached to the glycerolic backbone.

According to still further features in the described preferred embodiments the at least one phosphorous-containing moiety is a phosphate moiety being attached to the glycerolic backbone via a phosphodiester bond.

According to still further features in the described preferred embodiments reacting the purified fourth compound with the phosphorous-containing moiety comprises: providing the purified fourth compound having a free hydroxyl group; reacting the purified fourth compound with a reactive phosphorous-containing compound having a second reactive group and a third reactive group, the second reactive group being capable of reacting with the free hydroxyl group and a second reactive group, to thereby provide the first compound, the third compound, the purified third compound, the fourth compound or the purified fourth compound having a reactive phosphorous-containing group attached to the glycerolic backbone; and converting the reactive phosphorous-containing group to the phosphorous-containing moiety.

According to still further features in the described preferred embodiments the reactive phosphorous-containing compound is phosphorous oxychloride ($POCl_3$).

The present invention successfully addresses the shortcomings of the presently known configurations by providing novel synthetic routes that can be beneficially used in the scaled-up preparation of oxidized phospholipids.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

As used herein the term "mixture" describes a mixture that includes more than one substance and which can be in any form, for example, as a homogenous solution, a suspension, a dispersion, a biphasic solution and more.

As used in this application, the singular form "a", "an" and "the" include plural references unless the context clearly dictates otherwise.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein throughout, the terms "comprising", "including" and "containing" means that other steps and ingredients that do not affect the final result can be added. These terms encompass the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

The term "method" or "process" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

The term "phospholipid" is used herein to collectively describe compounds that include a non-polar lipid group and a highly polar end phosphate group. One particular and most prevalent in nature family of phospholipid compounds is the phosphoglycerides family of compounds. The term "phospholipid" is therefore typically used herein throughout to describe phosphoglycerides, unless otherwise indicated.

The term "phosphoglyceride" is therefore used herein to describe compounds having a glycerol backbone, one or more lipid moieties and one or more phosphate end group, which are attached to the glycerolic backbone. Most of the naturally-occurring glycerolipids include two lipid moieties attached to the sn-1 and sn-2 positions and one phosphate moiety attached to the sn-3 position of the glycerol backbone.

The term "oxidized phospholipid" is therefore used herein to describe a phospholipid, as well as a phosphoglyceride, which includes one or more oxidized moieties, as this term is described hereinbelow. Typically, in oxidized phospholipids, the oxidized moiety is included within a lipid moiety.

The term "glycerolipid" describes a compound having a glycerolic backbone and one or two lipid moieties attached thereto. The lipid moieties can be attached to the glycerol backbone via an ester and/or an ether bond.

As used herein, the term "lipid" describes a hydrocarbon residue having 3-30 carbon atoms. In naturally-occurring compounds, the lipids in phospholipids and glycerolipids are derived from fatty acids and are therefore attached to the backbone via an O-acyl(ester) bond. Herein, the lipid moiety can be attached to the backbone either via and ether or an ester bond.

As used herein, the terms "mono-esterified" and "di-esterified" with respect to phospholipids or glycerolipids, describe phospholipids or glycerolipids, either oxidized or non-oxidized, in which one or two of the lipid moieties, respectively, are attached to the glycerol backbone via an ester (e.g., O-fatty acyl) bond.

As used herein, the terms "mono-etherified" and "di-etherified" with respect to phospholipids or glycerolipids, describe phospholipids or glycerolipids, either oxidized or non-oxidized, in which one or two of the lipid moieties, respectively, are attached to the glycerol backbone via an ether bond.

The term "phosphoglycerol" describes a compound having a glycerolic backbone and a phosphate group attached to one position thereof.

The term "phosphoglycerides" describes a compound having a glycerolic backbone, one or two lipid moieties and a phosphate moiety attached thereto.

The term "mono-etherified phosphoglyceride" describes a phosphoglyceride, in which a lipid moiety is attached to the glycerolic backbone via an ether bond.

As used herein, the term "moiety" describes a functional substance or group which forms a part of a compound.

The term "residue" as is well known in the art, is used to described a major portion of a molecule that is linked to another molecule.

DESCRIPTION OF THE PREFERRED EMBODIMENTS

The present invention is of novel methods of preparing oxidized phospholipids which can be efficiently used for a scaled up production of such oxidized phospholipids. Specifically, the present invention is of novel methods of introducing an oxidized moiety to a compound having a glycerolic backbone and is further of novel methods of introducing a phosphorous-containing moiety to such a compound. The novel methods described herein are devoid of column chromatography and typically use commercially available and environmental friendly reactants.

The principles and operation of the novel synthetic methods according to the present invention may be better understood with reference to the accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

As discussed hereinabove, it has been recently reported that well-defined, synthetically prepared oxidized phospholipids can regulate the immune response to oxidized LDL and are thus highly effective in treating atherosclerosis and related diseases, as well as autoimmune diseases and inflammatory disorders. It has been further reported that generally, etherified oxidized phospholipids are superior to comparable esterified oxidized phospholipids as therapeutic agents.

These highly beneficial oxidized phospholipids typically include a glycerolic backbone, to which a lipid residue, a phosphate residue and an oxidized moiety-containing lipid residue are attached, as is described in detail, for example, in U.S. Pat. No. 6,838,452 and in WO 04/106486.

As is further discussed hereinabove, the presently known methods of preparing such well-defined synthetic oxidized phospholipids involve multi-step syntheses. While these multi-step syntheses were found to be relatively efficient, resulting in moderate to good yield, these methods are limited by the need to perform laborious isolation and purification procedures of the various intermediates formed throughout the syntheses. Particularly, these procedures typically involve techniques such as column chromatography, which, as is widely recognized by a skilled artisan, is industrially inapplicable, or at least inefficient in terms of costs, complexity and use of excessive amounts of organic solvents, which may be hazardous and requires special care of the waste disposal. The need to use column chromatography in these methods stems from the fact that the intermediates, as well as the final products formed during these multi-step syntheses, cannot be isolated and/or purified by more conventional techniques such as extraction, crystallization and the like.

Since such synthetically-prepared oxidized phospholipids exhibit exceptionally beneficial therapeutic activity, it is highly desired to prepare these compounds in a high level of purity. Furthermore, since the preparation of such oxidized phospholipids involves multi-step syntheses, purification of the intermediates is required in order to perform such a process is reasonable yields and with minimal amount of side products.

In a search for novel methods of preparing oxidized phospholipids, which could be efficiently utilized in the scaled-up production of these compounds, while circumventing the need to use laborious techniques such as column chromatography, the present inventors have designed and successfully practiced novel synthetic methodologies for introducing an oxidized moiety and/or a phosphate moiety to compounds that have a glycerolic backbone, which circumvent the disadvantageous use of column chromatography and which result in relatively high yield of pure compounds. The methods described herein further typically utilize commercially available, non-hazardous reactants, which further provides for the industrial applicability thereof.

The novel synthetic methodologies described herein can be divided as follows:

(i) a novel method of introducing an oxidized moiety to a compound having a glycerolic backbone, via introduction of an unsaturated moiety and oxidation of the unsaturated moiety, whereby upon said oxidation the oxidized moiety-containing compound is isolated and purified by means of a water-soluble adduct;

(ii) a novel method of introducing an oxidized moiety to a compound having a glycerolic backbone, via introduction of an unsaturated moiety and oxidation of the unsaturated moiety, whereby said oxidation is performed via an epoxide intermediate and in the presence of a selective protecting group;

(iii) a novel method of introducing an oxidized moiety to a compound having a glycerolic backbone, via introduction of an unsaturated moiety and oxidation of the unsaturated moiety, whereby said oxidation is performed directly and allows isolation and purification of the oxidized product by simple phase-separation means;

(iii) a novel method of introducing an oxidized moiety to a compound having a glycerolic backbone, via direct introduction of the oxidized moiety; and (iv) a novel method of introducing a phosphate moiety to a glycerolipid optionally having an oxidized or pre-oxidized moiety attached thereto, via introduction of a reactive phosphorous-containing group.

Due to the superior performance of oxidized phospholipids in which the oxidized moiety-containing residue is attached to the backbone via an ether bond, these methods are all directed for the attachment of the oxidized moiety-containing residue to the glycerolic backbone via an ether bond.

As is demonstrated in the Examples section that follows, using these methodologies, well-defined oxidized phospholipids, have been successfully prepared in relatively high yield and purity.

Thus, according to one aspect of the present invention there is provided a method of preparing a compound having a glycerolic backbone and at least one oxidized moiety-containing residue attached to the glycerolic backbone via an ether bond, which is devoid of column chromatography. The method, according to this aspect of the present invention, is effected by:

providing a first compound having a glycerolic backbone and at least one free hydroxyl group;

providing a second compound having at least one unsaturated bond and at least one reactive group capable of forming an ether bond with said free hydroxyl group;

reacting the first compound and the second compound to thereby obtain a third compound, which has a glycerolic backbone and an unsaturated bond-containing residue being attached to the glycerolic backbone via an ether bond;

isolating the third compound, to thereby obtain a purified third compound;

reacting the purified third compound with an oxidizing agent, to thereby obtain a fourth compound, which has a glycerolic backbone and an oxidized moiety-containing residue attached to the glycerolic backbone via an ether bond; and isolating the fourth compound to thereby obtain a purified fourth compound, thereby obtaining the compound having a glycerolic backbone and at least one oxidized moiety-containing residue attached to the glycerolic backbone via an ether bond.

As used herein throughout, the phrase "a compound having a glycerolic backbone", which is also referred to herein interchangeably as "a glycerolic compound", or a "glycerol compound" describes a compound that includes the following skeleton:

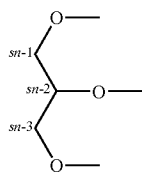

When the compound is glycerol, each of the glycerolic positions sn-1, sn-2 and sn-3 is substituted by a free hydroxyl group.

As used herein throughout, the phrases "oxidized moiety" and "an oxidized moiety-containing residue", which are used herein interchangeably, describe an organic moiety in which at least one of its carbon atoms is substituted by an oxygen atom. Examples, without limitation, include aldehyde, carboxylic acid, carboxylic ester, diol, acetal, and ketal. The phrases "a compound having an oxidized moiety-containing residue" and "an oxidized moiety-containing compound" are also used herein interchangeably.

The method according to this aspect of the present invention is based on introducing an unsaturated moiety to the glycerolic compound and subjecting the unsaturated bond to oxidative cleavage. However, while such a synthetic route has been employed in the presently known syntheses of glycerolic oxidized phospholipids, the present inventors have now designed and successfully practiced such a process in which the glycerolic compound that has an oxidized moiety attached thereto can be isolated and purified without using column chromatography.

Introduction of the unsaturated moiety to the glycerolic compound is typically performed using methods known in the art, such as described, for example, in U.S. Pat. No. 6,838,452.

Typically, a first compound, which has a glycerolic backbone and at least one free hydroxyl group, is selected as the starting material.

A compound that has an unsaturated moiety and a first reactive group, which is also referred to herein as the second compound, is obtained, either commercially or using methods known in the art, and is reacted with the glycerolic starting material.

The first reactive group is selected capable of reacting with the free hydroxyl group. Reacting with the free hydroxyl group so as to form an ether bond is typically performed via a nucleophilic mechanism and therefore the first reactive group is preferably characterized as a good leaving group and can be, for example, halide, sulfonate, and any other leaving group.

Preferably, the reactive group is halide and more preferably, it is bromide.

The second compound is preferably selected such that the unsaturated moiety is present at a terminus position thereof, so as to facilitate the oxidation reaction that follows. By "unsaturated moiety" it is meant herein a moiety that includes at least two carbon atoms that are linked therebetween by an unsaturated bond, e.g., a double bond or a triple bond, preferably a double bond.

Further preferably, the second compound comprises from 4 to 30 carbon atoms, more preferably from 4 to 27 carbon atoms, more preferably from 4 to 16 carbon atoms, more preferably from 4 to 10 carbon atoms, more preferably from 4 to 8 carbon atoms, and most preferably the second compound comprises 6 carbon atoms.

Reacting the first compound and the second compound described herein is typically performed in the presence of a base. Suitable bases for use in this context of the present invention include, without limitation, inorganic bases such as sodium hydroxide, lithium hydroxide, calcium hydroxide, barium hydroxide and potassium hydroxide.

Reacting the first compound and the second compound is typically performed in the presence of a solvent. Suitable solvents for use in this context of the present invention include, without limitation, non polar solvents such as petrol ether, hexane, benzene and toluene.

In cases where it is desired to perform the reaction selectively, namely, introducing the unsaturated moiety to a certain position of the glycerolic backbone, free hydroxyl group other than the reacting hydroxyl, if present, should be protected prior to the reaction.

Thus, in such cases, the method according to this aspect of the present invention optionally and preferably further comprises, prior to reacting the first compound and the second compound, protecting one or more additional free hydroxyl groups that may be present within the first compound.

Any of the known hydroxyl-protecting groups can be used in this context of the present invention. According to preferred embodiment of this aspect of the present invention, the protecting group is trityl.

Trityl is a bulky group, which typically serves as a selective protecting group, due to steric hindrance. Thus, while reacting a glycerolic compound that has more than one free hydroxyl group, typically, the trityl group would be reacted with the less hindered group.

As noted hereinabove and is further discussed in detail in U.S. Pat. No. 6,838,452 and in WO 04/106486, the position of the glycerolic backbone to which an oxidized moiety is attached affects the activity of the compound. It is therefore highly beneficial to perform the preparation of the glycerolic compounds described herein selectively, such that the oxidized moiety-containing residue would be attached to the desired position. As is further demonstrated in U.S. Pat. No. 6,838,452, oxidized phospholipids that have an oxidized moiety-containing residue attached to the sn-2 position of the glycerol backbone exhibit a superior performance.

To that end, the use of trityl group as the protecting group while introducing the above-described second compound to the glycerolic backbone is highly beneficial, since due to its bulkiness, protection of the hydroxyl end groups, at the sn-1 and/or an-3 positions would be effected, leaving the hydroxyl group at the sn-2 available for further substitutions.

Once the reaction between the first compound and the second compound is completed, a reaction mixture which contains a compound that has a glycerolic backbone and an unsaturated moiety-containing residue attached thereto via an ether bond is obtained. Such a compound is also referred to herein interchangeably as a third compound.

Depending on the starting material used, the third compound can further include one or more protecting groups, protecting free hydroxyl groups that may be present within the glycerolic backbone.

The third compound, either protected or deprotected, is then isolated from the reaction mixture and treated so as to obtain a purified compound.

In a preferred embodiment, isolating the third compound is performed by first collecting the formed third compound. Collecting the third compound is typically performed using conventional techniques such as extraction, removal of the solvent, filtration and the like, including any combination thereof. Once collected, the crude product is dissolved is a solvent, whereby the solvent is selected such that the third compound is soluble therein whereby impurities formed during the reaction between the first and the second compounds are insoluble therein.

The term "impurities" is used herein to describe any substance that is present in the final crude product and is not the product itself and include, for example, unreacted starting materials and side products.

Using such a solvent, a mixture that includes a solution of the third compound in such a solvent and insoluble substances is obtained. Suitable solvents for use in this context of the present invention include, without limitation, non-polar solvents such as petrol ether, hexane, benzene, heptane and toluene. Preferably, the solvent is petrol ether. Further preferably, the solvent is hexane.

The insoluble impurities are then removed from the mixture, preferably by filtration, the solvent is removed and a purified third compound is obtained while circumventing the need to use column chromatography in the purification procedure thereof.

The purified third compound is then reacted with an oxidizing agent, so as to oxidize the unsaturated moiety and thereby obtain a fourth compound, in which an oxidized moiety-containing residue is attached to the glycerolic backbone via an ether bond.

The oxidizing agent is selected depending on the desired oxidized moiety, as is detailed hereinbelow, and can be, for example, a peroxide, a periodate, a bismuthate, a permanganate, a chlorite, ozone, silver oxide, osmium tetraoxide and any combination thereof.

As used herein, the term "periodate" describes a compound having the formula $XIO_4$, wherein X can be hydrogen (for periodic acid) or a monovalent cation of a metal (e.g., sodium, potassium). A preferred periodate is sodium periodate ($NaIO_4$).

The term "bismuthate" describes a compound having the formula $XBiO_3$, wherein X can be hydrogen or a monovalent cation of a metal (e.g., sodium, potassium).

The term "permanganate" describes a compound having the formula $XMnO_4$, wherein X can be hydrogen or a monovalent cation of a metal (e.g., sodium, potassium). Preferred permanganate is potassium permanganate ($KMnO_4$).

The term "chlorite" describes a compound having the formula $XClO_2$, wherein X can be hydrogen or a monovalent cation of a metal (e.g., sodium, potassium). As used herein, the term "peroxide" include a compound having the formula R—O—O—H, wherein R can be hydrogen, alkyl, cycloalkyl, aryl, oxyalkyl, oxycycloalkyl and oxyaryl, as these terms are defined herein.

As used herein throughout, the term "alkyl" refers to a saturated aliphatic hydrocarbon including straight chain and branched chain groups. Preferably, the alkyl group has 1 to 20 carbon atoms.

A "cycloalkyl" group refers to an all-carbon monocyclic or fused ring (i.e., rings which share an adjacent pair of carbon atoms) group wherein one of more of the rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene, and adamantane.

An "aryl" group refers to an all-carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl.

The terms "oxyalkyl", "oxycycloalkyl" and "oxyaryl" describe an R'—C(=O)— group, whereby R' is alkyl, cycloalkyl or aryl, respectively, such that the peroxide is a peroxycarboxylic acid.

Preferably, the peroxide is hydrogen peroxide or a peroxycarboxylic acid (e.g., perbenzoic acid).

Thus, in one embodiment of this aspect of the present invention, the oxidized moiety is aldehyde and reacting the third compound with an oxidizing agent is performed by first converting the unsaturated moiety in the third compound to a diol moiety, preferably by means of an oxidizing agent, which is referred to herein as a first oxidizing agent; and then further oxidizing the diol moiety, by means of a second oxidizing agent, to the aldehyde moiety.

The first and the second oxidizing agents can be the same or different and can be, for example, a peroxide, a periodate, a bismuthate, a permanganate, a chlorite, ozone and any combination thereof.

In cases where the first and the second oxidizing agents are the same, and depending on the oxidizing agent used, converting the unsaturated moiety to a diol moiety and oxidizing the diol moiety can be performed simultaneously. Suitable oxidizing agents that can be used in this respect include oxidizing agents that are capable of inducing an oxidative cleavage of an unsaturated moiety such as, for example, ozone, osmium tetraoxide, and potassium permanganate.

In cases where the first and the second oxidizing agents are different, preferably the first oxidizing agent is a peroxide, such as hydrogen peroxide and the second oxidizing agent is, for example, a periodate or a bismuthate.

The reaction conditions at which the converting and oxidizing procedures are performed are determined in accordance with the oxidizing agent used.

In a preferred embodiment of this aspect of the present invention, the first and the second oxidizing agents are different and converting the unsaturated moiety to a diol moiety and oxidizing the diol moiety are performed sequentially. Further according to a preferred embodiment of this aspect of the present invention, once the diol is obtained, the protecting group, if present, is removed so as to obtained a compound having three or more free hydroxyl groups (herein, a triol). Such a compound can be easily purified, prior to its oxidation to an aldehyde, by means of crystallization, due to its unique chemical features, as is demonstrated in the Examples section the follows (see, Example 1). Once purified, selective protection the free hydroxyl group at the sn-1 and/or sn-3 positions can be effected, prior to the next synthetic step.

The thus formed aldehyde-containing glycerolic compound, is then isolated from the reaction mixture and purified.

In a preferred embodiment of this aspect of the present invention, the aldehyde is purified by means of forming a water-soluble adduct thereof.

Thus, once the reaction with the oxidizing agent(s) is completed, the aldehyde-containing fourth compound is collected using conventional techniques as described herein above and thereafter the crude product is converted into a water-soluble adduct thereof. By performing such a conversion in a biphasic system, an aqueous phase that contains the water-soluble adduct and an organic phase, which contains water-insoluble impurities are obtained. Since most of the side products and unreacted material formed during the oxidation reaction are organic substances, such substances are easily separated from the water-soluble adduct by collecting the aqueous phase. The aldehyde-containing compound is thereafter recovered by decomposing the water-soluble adduct.

Suitable water-soluble adducts that can be used in this context of the present invention are preferably obtained by reacting the aldehyde-containing compound with a Girard reagent.

Girard reagents are a family of substances that are capable of forming water-soluble hydrazone adducts with carbonyl-containing compounds, and thus allow the separation of carbonyl-containing compounds from other organic non-carbonylic compounds. Girard reagents are ionic derivatives of semicarbazide.

The T form is (Carboxymethyl)trimethylammonium chloride hydrazide:

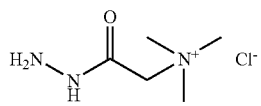

The D form is (Carboxymethyl)dimethylammonium chloride hydrazide:

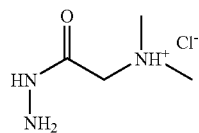

And the P form is 1-(Carboxylmethyl)pyridinium chloride hydrazide:

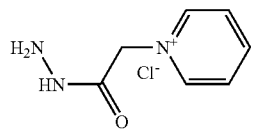

Thus, by converting the aldehyde-containing compound to a water-soluble adduct thereof with a Girard reagent, a purified fourth compound is easily and conveniently obtained, while avoiding the use of column chromatography.

In cases where the oxidized moiety is a carboxylic acid, reacting the third compound with an oxidizing agent can be performed by first providing an aldehyde-containing compound, optionally and preferably as described hereinabove, and further optionally and preferably, by providing a purified aldehyde-containing compound, using the methodology described hereinabove, and thereafter further oxidizing the aldehyde to carboxylic acid.

Oxidizing the aldehyde to a carboxylic acid is preferably performed by reacting the aldehyde with an oxidizing agent such as chlorite.

Alternatively, the unsaturated moiety can be oxidized to a carboxylic acid via an epoxide intermediate.

Thus, reacting the third compound with an oxidizing agent can be performed by converting the unsaturated moiety to epoxide, and converting the epoxide to the carboxylic acid. Preferably, converting the epoxide to a carboxylic acid is performed by converting the epoxide to diol and oxidizing the diol so as to obtain the carboxylic acid moiety.

Converting the third compound to an epoxide is preferably performed by reacting the third compound with a peroxide, as defined hereinabove, and more preferably with a peroxycarboxylic acid.

Converting the epoxide to diol is preferably performed by reacting the epoxide with perchloric acid (HClO$_4$). Alternatively, the epoxide is converted to diol by reacting it with sulfuric acid.

The diol is then converted to the carboxylic acid by reacting it with a third oxidizing agent. The third oxidizing agents can be selected from periodate, bithmutate, permanganate, chlorite and any combination thereof. Preferably, the diol is converted to the carboxylic acid by reacting it with a periodate, followed by a chlorite.

The fourth compound thus obtained, having a glycerolic backbone and a carboxylic acid-containing moiety attached thereto via an ether bond, in then purified, so as to obtain a purified product.

The present inventors have now surprisingly found that a fourth compound obtained via the epoxide intermediate can be easily purified, while avoiding the use of column chromatography, if a free hydroxyl group thereof is protected by a protecting group such as acetate, pivaloate or benzoate.

As mentioned hereinabove, a free hydroxyl group, if present in the glycerol backbone, is preferably protected, whereby a preferable, selective protecting group is trityl. However, since trityl is a large, bulky and non-polar moiety, its presence might, in some cases, complicate the isolation and purification procedures of the various intermediates and the final product.

The present inventors have now uncovered that limitations associated with the trityl group can be readily circumvented by: (i) isolating an aldehyde-containing compound via the formation of a water-soluble adduct thereof, as is widely described hereinabove; or (ii) replacing the trityl protecting group by a less bulky group, subsequent to the introduction of the second compound. In addition, as described hereinabove, when oxidizing the third compound comprises the formation of a diol, once the diol is forms, the trityl protecting group can be removed and the resulting triol can be isolated by means of crystallization.

Thus, according to a preferred embodiment of the present invention, the process further comprises, subsequent to the provision of the purified third compound and/or prior to reacting the third compound with an oxidizing agent: replacing the trityl group with a protecting group selected from the group consisting of acetate, pivaloate or benzoate.

Replacing the trityl protecting group is typically effected by removing the trityl group, so as to obtain a free hydroxyl group and protecting the hydroxyl group with the desired protecting group.

Protecting the hydroxyl group with an acetate group is readily performed by reacting the third compound with e.g., acetic anhydride. Protecting the hydroxyl group with a pivaloate group is readily performed by reacting the third compound with e.g., pivaloyl chloride. Protecting the hydroxyl group with a benzoate group is readily performed by reacting the third compound with e.g., benzoyl chloride.

Purifying a fourth compound, as described herein, which has an acetate, pivaloate or benzoate protecting group can be carried out by conventional extraction techniques, preferably while using silica gel during the extraction procedure.

As is demonstrated in the Examples section that follows (see, Example 2), it was found that preparing a glycerolic compound having an oxidized moiety-containing group attached thereto via an ether bond, via the formation of an epoxide-containing intermediate that has an acetate protecting group, resulted in highly purified compound and high reaction yield.

The present inventors have further uncovered that a fourth compound having a carboxylic acid as an oxidized moiety can be readily obtained by reacting the third compounds described herein with a mixture of a periodate and a permanganate as an oxidizing agent.

Converting the third compound directly to a carboxylic acid-containing compound is highly beneficial since it evidently render the entire process more efficient by reducing the number of synthetic steps and further circumvents the need to purify the intermediates formed during the oxidation process. In addition, the oxidizing agent utilized in this route comprises safe, non-hazardous agents.

Hence, according to the presently most preferred embodiment of the present invention, the oxidized moiety is carboxylic acid and oxidizing the third compound is effected by reacting the third compound with a mixture of a periodate and a permanganate.

Such a reaction is preferably performed in the presence of a base. Preferred bases that are suitable for use in this embodiment of the present invention include sodium carbonate and sodium bicarbonate.

In cases where the obtained fourth compound has a protecting group, as described hereinabove, once the fourth compound is obtained, isolated and optionally purified, the protecting group is removed.

In cases where the oxidized moiety is a carboxylic acid, the fourth compound can be readily isolated upon removal of the protecting group and obtaining a compound that has a carboxylic moiety and a hydroxy moiety.

Similarly to the procedure described hereinabove for isolating and purifying the third compound, the fourth compound can be readily purified by dissolving it in a solvent, whereby the solvent is selected such that the fourth compound is soluble therein whereby impurities formed during the oxidation process are insoluble therein.

Moreover, such a solvent can be selected such that the fourth compound is soluble therein whereby the protecting group is insoluble therein. Thus, performing the removal of the protecting group under conditions that involve such a solvent allows removing both the protecting group and the impurities formed during the oxidation reaction within the same synthetic step.

Using such a solvent, a mixture that includes a solution of the fourth compound in such a solvent and insoluble substances such as impurities and the protecting group is obtained. Suitable solvents for use in this context of the present invention include, without limitation, non-polar solvents such as petrol ether, hexane, benzene, heptane and toluene, semi-polar solvents such as ethyl acetate and mixtures thereof. Preferably, the solvent is petrol ether or hexane and/or a mixture of thereof with ethyl acetate.

The insoluble impurities are then removed from the mixture, preferably by filtration, the solvent is removed and a purified fourth compound is obtained while circumventing the need to use column chromatography in the purification procedure thereof and further circumventing the need for multiple purification procedures of the various intermediates formed.

In cases where the oxidized moiety is an ester, the process is effected by providing a carboxylic-acid containing compound and then converting the carboxylic acid to the ester. This can be readily carried out, using procedures well known in the art. Exemplary procedures are described in the Examples section that follows (see, for example, Examples 1, 6 and 7).

As is discussed hereinabove, compounds having a glycerolic backbone and at least one oxidized moiety-containing residue attached to the glycerolic backbone and further having a phosphorous-containing moiety attached to the glycerolic backbone, preferably a phosphate-containing moiety, are known as oxidized phospholipids and are highly beneficial in treating various conditions. Thus, the process described herein optionally and preferably further comprises introduction of such a phosphorous-containing moiety to the glycerolic backbone.

As used herein, the phrase "phosphorous-containing moiety" describes a moiety, as defined herein, which includes one or more phosphor atoms. Representative examples include, without limitation, phosphates, phosphonates, phosphines, phosphine oxides, phosphites, pyrophosphates and like.

As used herein the term "phosphonate" describes a —P(═O)(OR')(OR") group, where R' and R" are each independently hydrogen, or substituted or unsubstituted alkyl, cycloalkyl or aryl, as defined herein.

The term "phosphinyl" describes a —PR'R" group, with R' and R" as defined hereinabove.

The term "phosphine oxide" describes a —P(═O)(R')(R") end group or a —P(═O)(R')— linking group, as these phrases are defined hereinabove, with R' and R" as defined herein.

The term "pyrophosphate" describes an —O—P(═O)(OR')—O—P(═O)(OR')(OR")(OR''') group, with R', R" as defined herein, and R''' is defined as R' or R".

The term "phosphite" describes an —O—PH(═O)(OR') group, with R' as defined herein.

The term "phosphate" describes an —O—P(═O)$_2$(OR') group, with R' as defined herein.

The term "thiophosphate" describes an —O—P(═O)(═S)(OR') group, with R' as defined herein.

The introduction of a phosphorous-containing moiety to the glycerolic compound can be performed either prior to reacting the first compound and the second compound, prior to isolating the third compound, prior to reacting the third compound with the oxidizing agent, prior to isolating the fourth compound or subsequent to isolating the fourth compound, and can be performed using any of the methods known in the art.

Introduction of a phosphorous-containing moiety to a compound having a glycerolic compound is therefore performed by:

reacting any of the first compound, the third compound, the purified third compound, the fourth compound or the purified fourth compound described above, with a phosphorous-containing moiety, so as to obtain a compound having a glycerolic backbone and at least one oxidized moiety-containing residue attached to the glycerolic backbone and further having a phosphorous-containing moiety attached to the glycerolic backbone.

According to a preferred embodiment of the present invention, the phosphorous-containing moiety is a phosphate moiety which is attached to the glycerolic backbone via a phosphodiester bond.

Thus, the phosphorous-containing moiety can be, for example, phosphoric acid, phosphoryl choline, phosphoryl ethanolamine, phosphoryl serine, phosphoryl cardiolipin, phosphoryl inositol, ethylphosphocholine, phosphoryl-methanol, phosphorylethanol, phosphorylpropanol, phosphorylbutanol, phosphorylethanolamine-N-lactose, phosphoethanolamine-N-[methoxy(propylene glycol)], phosphoinositol-4-phosphate, phosphoinositol-4,5-biposphonate, pyrophosphate, phosphoethanolamine-diethylenetriamine-pentaacetate, dinitrophenyl-phosphoethanolamine and phosphoglycerol.

Preferably, the phosphorous-containing moiety is attached to the sn-3 position of the glycerolic backbone and thus, introduction of such a moiety is performed selectively, by appropriately protecting other free hydroxyl groups that are present in the reacting compound or deprotecting a protected hydroxyl group at the desired position.

In the presently known methods of preparing oxidized phospholipids, the phosphorous-containing moiety is typically introduced prior to the provision of an oxidized-moiety containing compound.

In addition, in cases where the phosphorous-containing moiety is phosphoryl choline, a widely used and beneficial moiety in such compounds, the presently known methods involve N-alkylation reactions, which involve hazardous and environmentally unfriendly reagents such as, for example, trimethylamine.

The present inventors have now uncovered that (i) a phosphorous-containing moiety can be readily introduced subsequent to the provision of an oxidized moiety-containing compound; and (ii) the introduction of the phosphorous-containing moiety can be efficiently performed via a reactive phosphorous-containing intermediate.

Based on the above, the present inventors have designed and successfully practiced a novel process for introducing a phosphorous-containing moiety to compounds having a glycerolic backbone and an oxidized moiety-containing residue attached thereto via an ether bond.

This process, combined with the process described above for preparing the oxidized moiety-containing compound, can be beneficially used for preparing the therapeutically beneficial oxidizes phospholipids described above.

Thus, according preferred embodiments of the present invention, the introduction of the phosphorous-containing moiety is performed subsequent to the production of the third compound or subsequent to the production of the fourth compound, with the latter being preferred. However, it should be noted that the process of introducing the phosphorous-containing moiety presented herein is also applicable at any other stage.

The introduction of a phosphorous-containing moiety to a glycerolic compound is therefore preferably effected, according to the present embodiments, by reacting a first compound, a third compound, a purified third compound, a fourth compound or a purified fourth compound as described above, which has a free hydroxyl group, with a reactive phosphorous-containing compound, so as to produce a compound having a reactive phosphorous-containing group; and converting the reactive phosphorous-containing group to the phosphorous-containing moiety.

The reactive phosphorous-containing compound is selected such that upon said reacting, a reactive phosphorous-containing group attached to the glycerolic backbone is obtained. The reactive phosphorous-containing compound is therefore selected as having a second reactive group and a third reactive group, whereby the second reactive group is selected capable of reacting with the free hydroxyl group and the third reactive group is selected capable of being converted to the phosphorous-containing moiety.

Reactive groups that are capable of reacting with a free hydroxyl groups include, for example halides, sulfonyl chlorides, acyl halides and the like.

Preferably the second reactive group is halide and more preferably it is chloride.

While as described hereinabove, preferable phosphorous-containing moieties are phosphate moieties, converting the phosphorous-containing compound to the desired phosphorous-containing moiety typically involves a formation of a phosphate-ester bond. Such a bond can be obtained, for example, by reacting a phosphoric derivative such as phosphoryl chloride with a hydroxy-containing moiety.

Thus, according to a preferred embodiment, the reactive phosphorous-containing compound is phosphorous oxychloride ($POCl_3$), such that the third and the second reactive groups are both chlorides and the compound having a phosphorous-containing reactive group has a glycerolic backbone and a phosphoryl chloride residue attached thereto.

Reacting the first compound, the third compound, the purified third compound, the fourth compound or the purified fourth compound with the phosphorous oxychloride is typically carried out in the presence of a base. Suitable bases include organic and inorganic bases, with organic bases being preferred. Thus, the reaction is preferably effected in presence of a base such as, for example, trialkylamine (e.g., triethylamine).

This reaction is further preferably carried out in the presence of a solvent, preferably a polar solvent such as THF.

The phosphoryl chloride-containing glycerolic containing compound obtained by the process described herein can be readily converted to any desired phosphorus-containing moiety and is therefore a highly beneficial intermediate.

Thus, for example, it can be converted to phosphoric acid by a simple hydrolysis thereof, as is exemplified in the Examples section that follows.

Alternatively, it can be reacted with a hydroxy-containing moiety, and optionally and preferably also with water, to thereby obtain other phosphate moieties.

Preferred phosphate moieties that are incorporated in therapeutic oxidized phospholipids (e.g., phosphoryl choline, phosphoryl ethanolamine) typically include an aminoalkyl group, which can be further N-alkylated.

Converting the phosphoryl chloride intermediate to such phosphate moieties can thus be readily performed by reaction with a derivative of the desired aminoalkyl group, selected capable of reacting with the third reactive group (being a chloride).

Thus, for example, aminoalkyl-containing phosphate moieties can be obtained by reacting the phosphoryl chloride intermediate with an aminoalcohol. If desired, the aminoalcohol can thereafter be further alkylated, so as to produce an N-alkylated aminoalkyl phosphate moiety, as in the case of a phosphoryl choline moiety.

Obtaining such an N-alkylated aminoalkyl phosphate moiety attached to a glycerolic backbone using the process described above is highly beneficial since it circumvents the need to use hazardous materials such as the trimethylamine typically used for obtaining such compounds.

As discussed hereinabove, the introduction of the phosphorous-containing moiety can be performed either prior to or subsequent to the introduction of an oxidized moiety-containing residue to the glycerolic compound. As is demonstrated in the Examples section that follows, a phosphoryl choline moiety was successfully introduced into glycerolic compounds having either an oxidized-moiety containing residue or an unsaturated-moiety containing residue (see, Examples 4 and 5). Thus, the process of introducing a phosphate moiety via a reactive phosphorous-containing intermediate presented herein can be performed either with glycerolic compounds having an oxidized or pre-oxidized moiety attached thereto via an ether bond.

In their search for improved methods for preparing oxidized phospholipids, the present inventors have further designed and practiced an additional process for preparing a glycerolic compound having an oxidized moiety attached thereto via an ether bond, which is effected by direct introduction of an oxidized moiety-containing residue to a glycerolic compound.

Hence, according to another aspect of the present invention, there is provided a method of preparing a compound having a glycerolic backbone and at least one oxidized moiety-containing residue attached to the glycerolic backbone via an ether bond, which is effected by:

providing a first compound having a glycerolic backbone and at least one free hydroxyl group, as described hereinabove;

providing a fifth compound having at least one oxidized moiety, as described hereinabove, and at least one fourth reactive group;

reacting the first compound and the fifth compound to thereby obtain a reaction mixture containing a sixth compound, being the compound having a glycerolic backbone and at least one oxidized moiety-containing residue attached to the glycerolic backbone via an ether bond; and isolating the compound having a glycerolic backbone and at least one oxidized moiety-containing residue attached to the glycerolic backbone via an ether bond.

The process according to this aspect of the present invention therefore involves the reaction of the first compound described hereinabove with a compound that has a reactive group that is capable of reacting with a free hydroxyl group of the first compound, referred to herein as a fourth reactive group, and an oxidized moiety. Such a compound is referred to herein as the fifth compound.

The oxidized moiety in the fifth compound can be any of the oxidized moieties described above, namely, an aldehyde, a diol, a carboxylic acid, an ester an acetal or a ketal. Optionally, the oxidized moiety can be a semi-oxidized moiety, namely, being readily converted to a desired oxidized moiety without reacting with an oxidizing agent. An example of such a semi-oxidized moiety is nitrile, which can be readily converted to a carboxylic acid by a simple hydrolysis.

The fourth reactive group in the fifth compound is as described herein for the first reactive group and is preferably a halide and more preferably a bromide.

Reacting the first compound and the fifth compound is preferably effected in the presence of a base. Relatively strong inorganic bases such as, for example, sodium hydride, potassium hydroxide, lithium aluminum hydride, sodium amide, sodium hydroxide and any mixture thereof are preferred.

Under such reaction conditions, a fifth compound which has 4 or 5 carbon atoms might be cyclized during the reaction, thus adversely affecting the reaction efficiency.

Thus, preferably, the fifth compound preferably has less than 4 or more than 5 carbon atoms.

As described hereinabove, in cases where the first compound has more than one hydroxyl group attached thereto, the hydroxyl group is optionally and preferably protected by a protecting group, prior to reacting the first and the fifth compounds.

Once the sixth compound is obtained, the protecting group can be removed and the compound is purified using conventional purification methods.

The process according to this aspect of the present invention is highly beneficial since it enables to prepare the described oxidized moiety-containing compound in a one-step synthesis.

Using this process, oxidized phospholipids can be readily obtained by introducing a phosphorous-containing moiety, a described in detail hereinabove, either prior to or subsequent to the reaction with the fifth compound. The introduction of the phosphorous-containing moiety is preferably performed using the process presented hereinabove.

In any of the processes described herein, the first compound can include an alkylene chain attached thereto. Preferably, the alkylene chain is attached to the sn-1 position of the first compound.

The alkylene chain can be attached to the glycerolic compound by, for example, an ester bond or an ether bond. Preferably, the alkylene chain is attached via an ether bond, such that the final product is a dietherified glycerolic compound.

Thus, in each of the processes described herein, the first compound is a glycerolipid, as defined herein and preferably, a mono-etherified glycerolipid in which the lipid moiety is attached to the sn-1 position of the glycerol. Such a first compound therefore has one free hydroxyl group, which, as described hereinabove, is preferably protected prior to any reaction.

Thus, the first compound can be, for example, a glycerol, a glycerolipid, a mono-etherified glycerolipid, a di-etherified glycerolipid, a phosphoglycerol, a phosphoglyceride, a mono-etherified phosphoglyceride and a lysolechitin.

As is discussed in detail hereinabove, the position at which the oxidized moiety-containing residue is attached to the glycerolic backbone affects the activity of the resulting compounds and thus, as is further discussed hereinabove, it is preferably to perform the reaction selectively.

Preferably, in any of the processes described herein the oxidized moiety-containing residue is attached to the sn-2 position of the compound. Thus, by appropriately selecting and/or protecting the first compound, selective attachment of the oxidized moiety-containing residue is performed.

In a preferred embodiment of the present invention, the first compound therefore has the following general formula I:

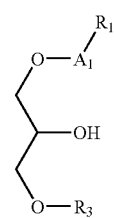

Formula I wherein:

$A_1$ is absent or is selected from the group consisting of $CH_2$, CH=CH and C=O;

$R_1$ is selected from the group consisting of H and a hydrocarbon chain having from 1 to 30 carbon atoms; and $R_3$ is selected from the group consisting of hydrogen, alkyl, aryl, phosphoric acid, phosphoryl choline, phosphoryl ethanolamine, phosphoryl serine, phosphatidyl choline, phosphatidyl ethanolamine, phosphatidyl serine, phosphatidyl cardiolipin, phosphatidyl inositol, phosphoryl cardiolipin, phosphoryl inositol, ethylphosphocholine, phosphorylmethanol, phosphorylethanol, phosphorylpropanol, phosphorylbutanol, phosphorylethanolamine-N-lactose, phosphoethanolamine-N-[methoxy(propylene glycol)], phosphoinositol-4-phosphate, phosphoinositol-4,5-biposphonate, pyrophosphate, phosphoethanolamine-diethylenetriamine-pentaacetate, dinitrophenyl-phosphoethanolamine, phosphoglycerol.

Using any of the processes described hereinabove, a compound having the following general Formula II can thus be obtained:

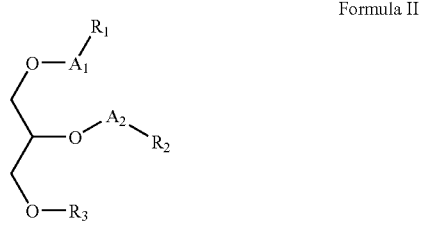

Formula II wherein:

$A_1$ is selected from the group consisting of $CH_2$, $CH=CH$ and $C=O$ and is preferably $CH_2$;

$A_2$ is $CH_2$;

$R_1$ is an alkyl having 1-30 carbon atoms;

$R_2$ is

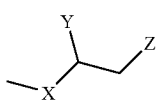

whereas:

X is an alkyl chain having 1-24 carbon atoms;

Y is selected from the group consisting of hydrogen, hydroxy, alkyl, alkoxy, halide, acetoxy and an aromatic functional group; and Z is selected from the group consisting of:

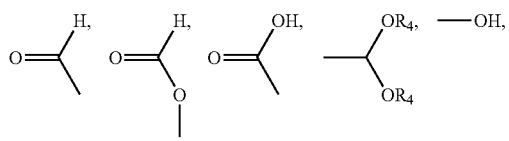

with $R_4$ being an alkyl or aryl; and $R_3$ is selected from the group consisting of hydrogen, alkyl, aryl, phosphoric acid, phosphoryl choline, phosphoryl ethanolamine, phosphoryl serine, phosphatidyl choline, phosphatidyl ethanolamine, phosphatidyl serine, phosphatidyl cardiolipin, phosphatidyl inositol, phosphoryl cardiolipin, phosphoryl inositol, ethylphosphocholine, phosphorylmethanol, phosphorylethanol, phosphorylpropanol, phosphorylbutanol, phosphorylethanolamine-N-lactose, phosphoethanolamine-N-[methoxy(propylene glycol)], phosphoinositol-4-phosphate, phosphoinositol-4,5-biposphonate, pyrophosphate, phosphoethanolamine-diethylenetriamine-pentaacetate, dinitrophenyl-phosphoethanolamine, phosphoglycerol.

As is demonstrated in the Examples section that follows, the above-described processes can be used for producing oxidized phospholipids, and particularly therapeutically beneficial oxidized phospholipids such as 1-hexadecyl-2-(4'-carboxy)butyl-3-phosphocholine (also known in the art and referred to herein as CI-201). For example, using the process described in Example 6 hereinbelow, 1-Hexadecyl-2-(4'-carboxy)butyl-3-phosphocholine was produced in an industrial scale of dozens of Kg.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

General Synthetic Pathways:

According to the teachings of the present invention, several general synthetic concepts are used for preparing oxidized phospholipids, as follows:

(i) Preparation of a glycerolipid compound having at least one oxidized moiety-containing residue attached thereto via an ether bond, by attachment of an unsaturated residue to a glycerolipid and oxidizing the unsaturated bond, while using a Girard reagent and/or crystallization of a triol-containing compound for isolating the oxidized product, as exemplified in Example 1 and Schemes I-V;

(ii) Preparation of a glycerolipid compound having at least one oxidized moiety-containing residue attached thereto via an ether bond, by attachment of an unsaturated residue to a glycerolipid and oxidizing the unsaturated bond via an epoxide intermediate, while using an acetoxy protecting group, as exemplified in Example 2 and Schemes VI-X;

(iii) Preparation of a glycerolipid compound having at least one oxidized moiety-containing residue attached thereto via an ether bond by direct introduction of an oxidized moiety-containing compound, as exemplified in Example 3 and Scheme XI; and (iv) Introduction of a reactive phosphorous-containing moiety to a glycerolipid compound having one or two oxidized (or pre-oxidized) moiety-containing residues attached thereto via an ether bond using a reactive phosphorous-containing compound (for example, phosphorous dichloride) for forming a reactive intermediate, as exemplified in Examples 4 and 5 and Schemes XII-XIV.

Example 1

Preparation of rac-1-hexadecyl-2-(5'-pentanoic methyl ester)-glycerol using periodate and a Girard T reagent In this example, an unsaturated moiety is introduced into a glycerolic backbone and is thereafter oxidized by means of formic acid, hydrogen peroxide and periodate. Then thus formed oxidized product is purified by means of a Girard reagent.

As a representative example, the preparation of rac-1-hexadecyl-2-(5'-pentanoic methyl ester)-glycerol is hereby described.

rac-1-Hexadecyl-2-(5'-pentanoic methyl ester)-glycerol is prepared in accordance with the teachings of the present invention, as is described in Schemes I through V below.

1-Hexadecyl-3-tritylglycerol was prepared as described in U.S. Pat. No. 6,838,452. In brief, D-acetone glycerol (4 grams), powdered potassium hydroxide (approximately 10 grams) and hexadecyl bromide (9.3 grams) in benzene (100 ml) were stirred and refluxed for 5 hours, while removing the water formed by azeotropic distillation (compare W. J. Baumann and H. K. Mangold, J. Org. Chem. 29: 3055, 1964 and F. Paltauf, Monatsh. 99:1277, 1968). The volume of the solvent was gradually reduced to about 20 ml, and the resulting mixture was cooled to room temperature and dissolved in ether (100 ml). The resulting solution was washed with water (2×50 ml), and the solvent was removed under reduced pressure. A 100 ml mixture of 90:10:5 methanol:water:concentrated hydrochloric acid was added to the residue and the mixture was refluxed for 10 minutes. The product was extracted with ether (200 ml) and was washed consecutively with water (50 ml), 10% sodium hydroxide (20 ml) and again with water (volumes of 20 ml) until neutral. The solvent was removed under reduced pressure and the product (8.8 grams) was crystallized from hexane to give 7.4 grams of pure 1-hexadecyl-glycerol.

1-Hexadecyloxy-glycerol (7.9 grams), triphenylchloromethane (8.4 grams) and dry pyridine (40 ml) were heated at 100° C. for 12 hours. After cooling, 300 ml of ether and 150 ml of ice-cold water were added, and the reaction mixture was transferred to a separatory funnel. The organic phase was washed consecutively with 50 ml of ice water, 1% potassium carbonate solution (until basic) and 50 ml of water, then dried over anhydrous sodium sulfate. The solvent was evaporated, the residue was dissolved in 150 ml of warm petroleum ether and the resulting solution was cooled at 4° C. overnight. After filtration of the precipitate, the filtrate was evaporated and the residue was recrystallized from 20 ml of ethyl acetate at −30° C., yielding 8.2 grams of 1-Hexadecyl-3-tritylglycerol, melting point 49° C.

As depicted in Scheme 1,1-hexadecyl-3-tritylglycerol (14.78 grams, 0.0265 mole), 6-bromo-1-hexene (4.85 grams) and powdered potassium hydroxide (approximately 10 grams) in hexane (200 ml) were stirred and refluxed for 6 hours, while removing the water formed by azeotropic distillation. The reaction mixture was cooled to room temperature, washed with water (3×100 ml), and the solvent removed under reduced pressure. The residue was dissolved in chloroform (50 ml) and purified by filtration over silica gel 60 (12.5 grams). The chloroform was removed under reduced pressure and the residue dissolved in petroleum ether (100 ml). The solution was kept at 4° C. for overnight, during which precipitation of byproducts occurred. Filtration and removal of the solvent under reduced pressure gave 12.15 grams (0.0190 mole) of 1-Hexadecyl-2-(5'-hexenyl)-3-tritylglycerol (72% yield).

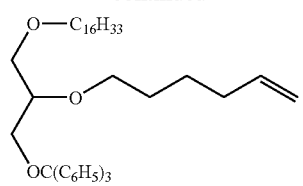

1-Hexadecyl-2-(5'-hexenyl)-3-tritylglycerol (19.80 g) was dissolved in formic acid (100 ml). The yellow solution was stirred at room temperature for 2 hours and was then cooled in ice bath. Hydrogen peroxide 33% (25 ml) was added dropwise to ice-cooled solution during 50 minutes. The color of the reaction mixture almost immediately changed from yellow to white. After the addition was completed stirring in ice-bath was continued for additional 4 hours. The reaction mixture was thereafter poured on ice (150 grams) and extracted with ether (3×100 ml). The orange etheral solution was washed with water (100 ml) and the solvent was removed under reduced pressure. The residue was dissolved in dichloromethane (150 ml), washed with saturated aqueous solution of sodium bicarbonate (100 ml) and the solvent was removed under reduced pressure. The residue was then dissolved in hot hexane (250 ml). Precipitation of white compound was obtained immediately. The solution was maintained at 4° C. overnight. Filtration of the precipitate (0.53 grams), followed by removal of the solvent under reduced pressure gave 20.03 grams of yellow oily residue. This residue was dissolved in iso-propanol (200 ml) and aqueous solution of sodium hydroxide (17 grams in 50 ml of water) was added. The resulting solution was heated to 90° C. for 2 hours and was then cooled and poured on ice (150 grams). Then the mixture was extracted with dichloromethane (3×100 ml), the organic phase was washed with water (100 ml) and saturated aqueous solution of sodium dihydrogen phosphate and was dried over anhydrous $Na_2SO_4$. After removal of the solvent under reduced pressure 10.77 grams of crude product were obtained. The crude product was then dissolved in 80% methanol (100 ml) and the solution was kept at 4° C. overnight. Filtration of the precipitate and removal of most of the solvent under reduced pressure. Extraction with dichloromethane (3×100 ml), drying over anhydrous $Na_2SO_4$ and removing of the solvent under reduced pressure Recrystallization from hexane (250 ml) gave 7.44 grams of pure 1-Hexadecyl-2-(5',6' dihydroxy-hexanyl)-glycerol.

Scheme I

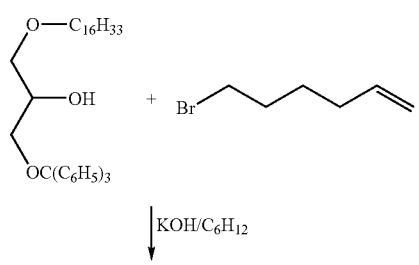

↓ KOH/C₆H₁₂

Scheme II

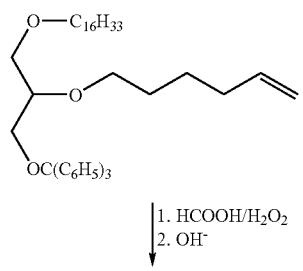

↓ 1. HCOOH/H₂O₂
  2. OH⁻

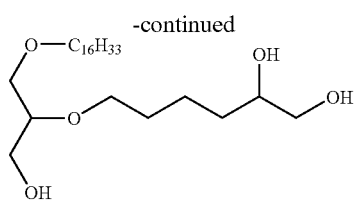

As depicted in Scheme III, 1-Hexadecyl-2-(5',6'-dihydroxy-hexanyl)-glycerol (7.84 grams) was dissolved in isopropanol (50 ml) and water (12 ml). NaIO$_4$ (9 grams) was added and the reaction mixture was stirred at room temperature for 3 hours. Water (50 ml) was added and the reaction mixture extracted with chloroform (3×50 ml), dried over anhydrous Na$_2$SO$_4$, filtered and the solvent removed under reduced pressure yielding 5.56 grams. The crude product was dissolved in ethanol (60 ml) and glacial acetic acid (2.3 grams). Girard's reagent T (5.6 grams) was added and the reaction mixture was refluxed for 2 hours. The reaction mixture was cooled in ice-bath, alkaline solution (2.3 grams in 45 ml water) was added and the mixture was extracted with ether (3×25 ml). The etheral phase was washed with water and the water combined with the alkaline phase. The aqueous phase was acidified with concentrated HCl (4.4 ml) and extracted with ether (3×25 ml). Washing with water, saturated aqueous sodium bicarbonate (3×25 ml), water (2×25 ml), drying over anhydrous Na$_2$SO$_4$ and removal of the solvent under reduced pressure gave 1.95 grams (0.0049 mol) of 1-Hexadecyl-2-(5'-oxo-pentanyl)-glycerol (26.9% yield).

Scheme III

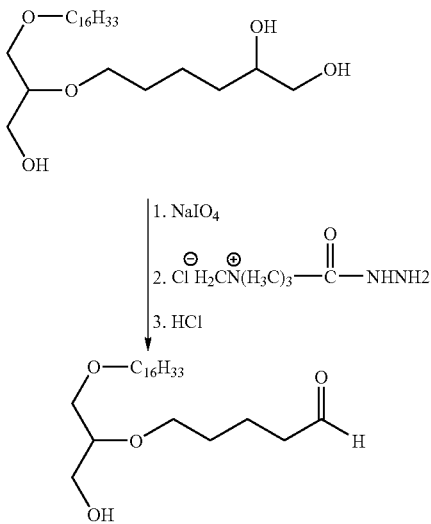

As depicted in Scheme IV, 1-Hexadecyl-2-(5'-oxopentyl)-glycerol (4.80 grams) was dissolved in dry triethylamine (57 ml). Acetic anhydride (20 ml) was added and the reaction mixture was stirred at room temperature for 2.5 hours. The reaction mixture was poured on ice (100 grams) and extracted with dichloromethane (3×100 ml). The organic phase was washed consecutively with water (100 ml), diluted hydrochloric acid (100 ml), water (100 ml), saturated aqueous sodium bicarbonate (100 ml) and again with water (100 ml) and was then dried over anhydrous sodium sulfate. The solvent removed under reduced pressure to give 4.54 grams of 1-Hexadecyl-2-(5'-oxopentyl)-3-acetate glycerol (yield 86%).

1-Hexadecyl-2-(5'-oxopentyl)-3-acetate glycerol (3.94 grams) was dissolved in t-butanol (75 ml). Sodium chlorite (6.85 grams) and sodium dihydrogen phosphate dihydrate (15.50 grams) were dissolved in water (75 ml). The aqueous solution was added to the alcoholic solution and the reaction mixture was e at room temperature for 4 hours. The reaction mixture was then transferred to separatory funnel and extracted with dichloromethane (3×100 ml). The combined organic phase was washed with water (2×100 ml) and the solvent was removed under reduced pressure. The residue was dissolved in a mixture of methanol (80 ml) and 10% aqueous NaOH (20 ml) and the solution was stirred at room temperature overnight. The methanolic solution was extracted with a mixture of toluene and hexane (1:1) (2×50 ml), cooled in ice-bath and HCl conc. was added slowly to reach pH 5-6. The solution was then extracted with dichloromethane (2×100 ml). The combined organic phase was washed with water (100 ml), dried over anhydrous Na$_2$SO$_4$ and the solvent was removed under reduced pressure to give 2.07 grams of a crude product. Recrystallization from hexane (20 ml) gave 1.30 grams of pure 1-Hexadecyl-2-(4'-carboxy) butyl-glycerol (yield 35%).

Scheme IV

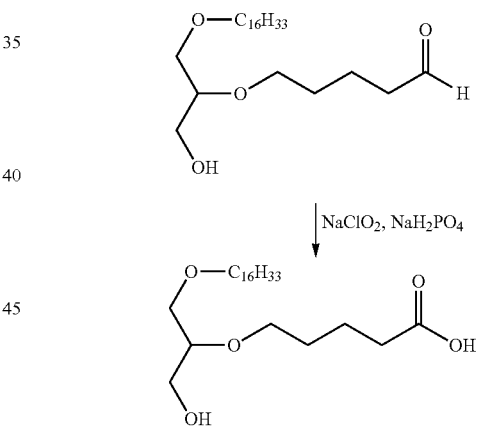

As depicted in Scheme V, to the residue methanol (100 ml) and 10% aqueous NaOH (20 ml) were added and the resulting solution stirred at room temperature for 2 hours. The solution was extracted with mixture of petroleum ether/toluene (1:1, v/v) and the methanolic phase acidified to pH=0 with concentrated HCl and then extracted with chloroform (3×50 ml). The solvent was removed under reduced pressure and the residue was dissolved in methanol (20 ml). Concentrated HCl (3 drops) was added and the solution stirred at room temperature over night followed by extraction with chloroform (2×25 ml). The combined chloroform phase was washed with water (2×50 ml), dried over anhydrous Na$_2$SO$_4$ and the solvent removed under reduced pressure yielding 0.77 gram (0.00179 mol) of rac-1-Hexadecyl-2-(5'-pentanoic methyl ester)-glycerol (96.7% yield).

Scheme V

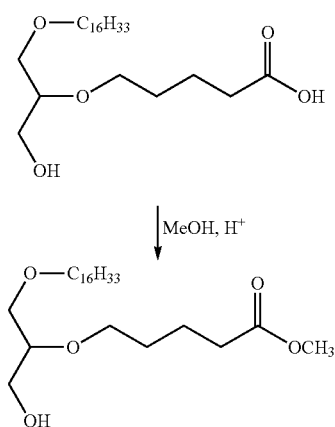

Example 2

Preparation of rac-1-hexadecyl-2-(5'-pentanoic methyl ester)-glycerol using periodate and an acetate protecting group In this example, an unsaturated moiety is introduced into a glycerolic backbone and is thereafter oxidized to an ester via an epoxide by means of acetic anhydride, 4-chlorobenzoperoxoic acid, $HClO_4$ periodate and methanol. Efficient isolation of the intermediates is performed by carrying out the reactions while using an acetate protecting group As a representative example, the preparation of rac-1-hexadecyl-2-(5'-pentanoic methyl ester)-glycerol is hereby described.

rac-1-Hexadecyl-2-(5'-pentanoic methyl ester)-glycerol is prepared in accordance with the teachings of the present invention, as is described in Schemes VI through X below.

As depicted in Scheme VI below, 1-Hexadecyl-2-(5'-hexenyl)-3-tritylglycerol, prepared as described in Example 1 above (4.90 grams) was dissolved in a mixture of methanol (30 ml) and concentrated hydrochloric acid (3 ml) and the resulting solution was heated to reflux for 4 hours. The reaction mixture was cooled to room temperature, poured on ice (100 grams) and extracted with chloroform (3×100 ml). The organic phase was washed with water (100 ml), aqueous sodium bicarbonate (100 ml) and again with water (100 ml). Thereafter the organic phase was dried over anhydrous $Na_2SO_4$, filtered and the solvent was removed to afford 3.75 grams of a residue. The residue was dissolved in n-hexane and kept at 4° C. overnight. Filtration of the precipitate and removal of the solvent gave 3.17 grams, which were dissolved in chloroform (200 ml) and added to silica gel (45 grams). This solution was filtered and the silica gel extracted again with mixture of chloroform:methanol (200 ml, 9:1) and chloroform:methanol (200 ml, 1:1). The two last extracts were combined and the solvent removed under reduced pressure to afford 2.56 grams of 1-Hexadecyl-2-(5'-hexenyl)-glycerol (84% yield).

Scheme VI

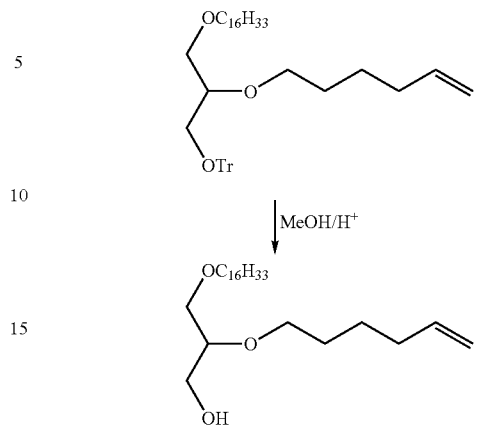

As depicted in Scheme VII below, dry pyridine (5 ml) and acetic anhydride (3 ml) were added to the resulting 1-Hexadecyl-2-(5'-hexenyl)-glycerol and the reaction mixture heated at 70° C. for 2 hours. The reaction mixture was poured on ice (25 gram) and extracted with hexane (3×25 ml). The extract was washed successively with water (25 ml), aqueous diluted sulfuric acid (25 ml), water (25 ml), aqueous sodium bicarbonate (25 ml) and water. After drying over anhydrous $Na_2SO_4$, filtration and removal of the solvent 2.60 grams were obtained. The residue was dissolved in dichloromethane (50 ml) and 3-chloroperbenzoic acid (3.84 grams) added, and the reaction mixture was stirred at room temperature for over night. The solvent was reduced to about 20 ml under reduced pressure and n-hexane (100 ml) was added. After filtration the solvent was evaporated to dryness. The residue was dissolved in n-hexane (100 ml), alkaline solution (0.4 grams NaOH in 50 ml of water) was added and the phases were separated. Washing of the organic phase successively with water (25 ml), aqueous sodium bicarbonate (25 ml), water (25 ml), drying over anhydrous $Na_2SO_4$, filtration and removal of the solvent afforded 2.40 grams of 1-Hexadecyl-2-(5',6'-epoxyhexanyl)-3-acetate glycerol (82% yield).

Scheme VII

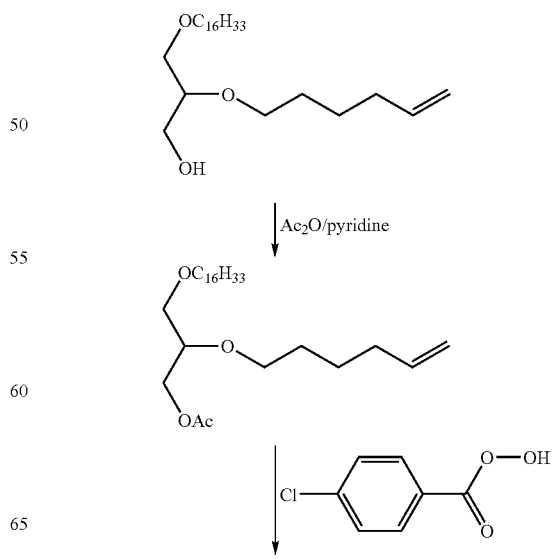

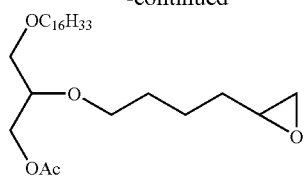

As depicted in Scheme VIII below, 1-Hexadecyl-2-(5',6'-epoxyhexanyl)-3-acetate glycerol was dissolved in acetone (50 ml). 7% HClO$_4$ (5 ml) was added and the reaction mixture stirred at room temperature for 40 hours. Water (50 ml) was added and the reaction mixture extracted with chloroform (3×50 ml). Washing of the organic phase successively with water (25 ml), aqueous sodium bicarbonate (25 ml), water (25 ml), drying over anhydrous Na$_2$SO$_4$, filtration and removal of the solvent gave 2.29 grams of oily residue. The residue was dissolved in chloroform (200 ml) and added to silica gel (30 grams). This solution was filtered and the silica gel extracted again with mixture of chloroform:methanol (200 ml, 8:2). In the second extract after solvent removed under reduced pressure 1.45 grams of 1-Hexadecyl-2-(5',6'-dihydroxyhexanyl)-3-acetate glycerol were obtained.

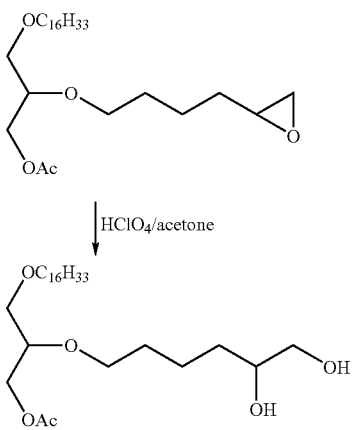

As depicted in Scheme IX below, 1-Hexadecyl-2-(5',6'-dihydroxyhexanyl)-3-acetate glycerol was dissolved in isopropanol (50 ml). Aqueous solution of sodium periodate (1.45 grams in 50 ml of water) was added and the reaction mixture stirred at room temperature for 2 hours. The reaction mixture was extracted with chloroform (3×50 ml), dried over anhydrous Na$_2$SO$_4$, filtered and the solvent removed under reduced pressure yielding 0.96 gram. The residue was dissolved in t-butanol (50 ml) and aqueous solution (50 ml) of sodium chlorite (1.66 grams) and sodium dihydrogen phosphate dihydrate (3.76 grams) was added. The reaction mixture was stirred at room temperature for 4 hours, extracted with chloroform (2×50 ml) and the solvent removed under reduced pressure. The residue was dissolved in mixture of chloroform:hexane (200 ml, 1:1) and added to silica gel (15 grams). The solution was filtered and the silica gel extracted again with chloroform (200 ml) and chloroform:methanol (200 ml, 9:1). The solvent from the last extract was removed under reduced pressure to give 0.92 grams of 1-Hexadecyl-2-(4'-carboxybutyl)-3-acetate glycerol.

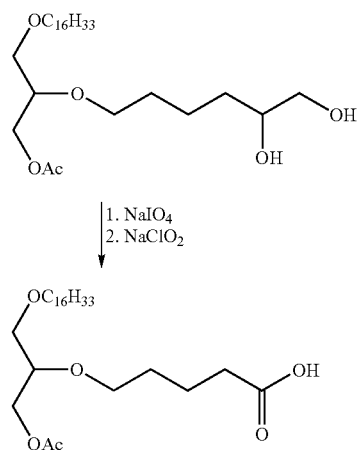

As depicted in Scheme X below, 1-Hexadecyl-2-(4'-carboxybutyl)-3-acetate glycerol dissolved in 50 ml of an 8:2 mixture of methanol and 10% aqueous NaOH and the reaction mixture is stirred vigorously at room temperature overnight. The reaction mixture is extracted with mixture of toluene:petroleum ether (2×25 ml, 1:1). The methanolic phase is acidified with concentrated HCl until reaching pH of about 0, and then extracted with chloroform (2×25 ml). The solvent was removed under reduced pressure and the residue was dissolved in methanol (10 ml). Concentrated HCl (2 drops) is added and the solution is stirred at room temperature over night followed by extraction with chloroform (2×25 ml), successive washing of the organic phase with water (25 ml), followed by washing with aqueous sodium bicarbonate (25 ml), water (25 ml), followed by drying over anhydrous Na$_2$SO$_4$, filtration and removal of the solvent to afford 0.86 grams of pure rac-1-Hexadecyl-2-(5'-pentanoic methyl ester)-glycerol.

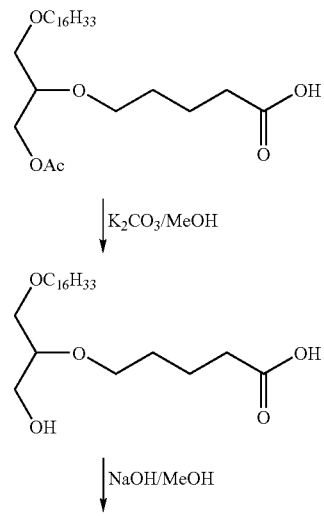

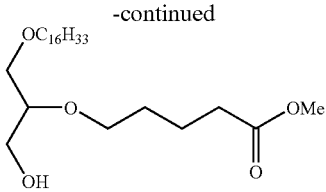

Example 3

Preparation of rac-1-hexadecyl-2-(5'-pentanoic ethyl ester)-glycerol by direct introduction of an oxidized moiety —Route I rac-1-Hexadecyl-2-(5'-pentanoic ethyl ester)-glycerol is prepared in accordance with the teachings of the present invention, as is described in Scheme XI below.

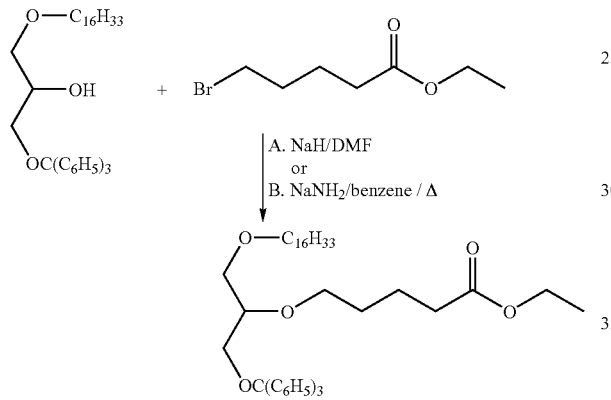

Scheme XI

1-Hexadecyl-3-tritylglycerol is prepared as described, for example, in Example 1 above or as described in U.S. Pat. No. 6,838,425.

To a three-necked flask equipped with a magnetic stirrer, 1.0 gram (1.8 mmole) 1-hexadecyl-3-tritylglycerol, 0.78 gram (3.6 mmole) 5-bromovaleric acid ethyl ester and 75 ml dimethylformamide (DMF) are added. To the stirred solution, 0.20 gram (5 mmole) NaH (60% dispersion in mineral oil) dissolved in 25 ml dimethylformamide are added dropwise over 15 minutes and stirring is continued for an additional 1 hour until the reaction is completed. Water was added (50 ml) and the mixture extracted with ether (3×50 ml). The organic phase was dried over anhydrous $Na_2SO_4$ and the solvent removed under reduced pressure. The crude product was purified over column chromatography on silica gel.

Deprotection of the trityl group as described hereinabove gave the final product.

Example 4

Introduction of a phosphorous-containing moiety to glycerolipid compound

According to the teachings of the present invention, a reactive phosphorous-containing moiety is introduced into a glycerolipid compound having one or two oxidized (or pre-oxidized) moiety-containing residues attached thereto via an ether bond. The introduction of the reactive phosphorous-containing moiety is performed using a phosphorous-containing compound such as, for example, phosphorous oxychloride). Optionally, subsequent to the introduction of the reactive phosphorous-containing moiety, the reactive phosphorous-containing moiety is converted to a phosphate moiety.

Preparation of rac-1-hexadecyl-2-(5'-hexenyl)-3-dichlorophosphate:

As a representative example, rac-1-Hexadecyl-2-(5'-hexenyl)-3-dichlorophosphate was prepared in accordance with the teachings of the present invention, as is described in scheme XII below.

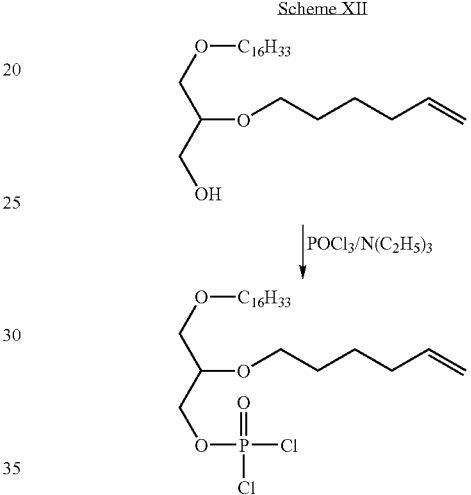

Scheme XII

Thus, 0.24 ml (0.39 gram, 2.53 mmole) $POCl_3$ and 10 ml tetrahydrofuran (THF) are placed in an ice-cooled three-necked flask equipped with a magnetic stirrer. To the stirred solution was added dropwise, over 25 minutes, a mixture of 0.87 gram (2.2 mmole) rac-1-Hexadecyl-2-(5'-hexenyl)-glycerol, 0.34 ml (0.25 gram, 2.44 mmole) triethylamine and 50 ml tetrahydrofuran (THF) and stirring is continued for an additional 10 minutes in an ice-bath and further continued for 45 minutes at 23° C.

The rac-1-Hexadecyl-2-(5'-hexenyl)-3-dichlorophosphate can be hydrolyzed, to thereby produce the corresponding phosphatidic acid, as follows:

One gram of ice is added to the reaction mixture and stirring is continued for 30 minutes. Water (50 ml) is then added and the product is extracted with mixture of chloroform:MeOH (2:1, v/v, 3×25 ml). The organic phase is washed with water and the solvent removed under reduced pressure.

Alternatively, the rac-1-Hexadecyl-2-(5'-hexenyl)-3-dichlorophosphate can be reacted with various alkylamine derivatives, to thereby produce a phosphoglyceride, as is exemplified below.

Preparation of rac-1-hexadecyl-2-(5'-hexenyl)-3-phosphoethanolamine from rac-1-Hexadecyl-2-(5'-hexenyl)-3-dichlorophosphate:

rac-1-hexadecyl-2-(5'-hexenyl)-3-phosphoethanolamine was prepared in accordance with the teachings of the present invention, as is described in scheme XIII Scheme XIII

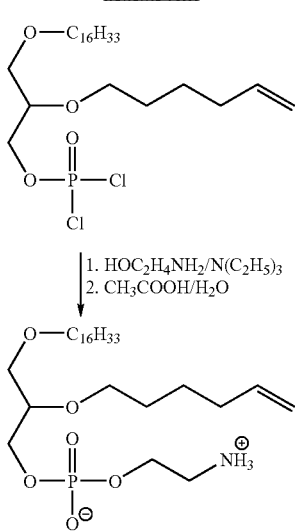

A solution of rac-1-hexadecyl-2-(5'-hexenyl)-3-dichlorophosphate in THF prepared as described immediately hereinabove in Example 2 was cooled in an ice bath. To the solution was added dropwise over a period of 10 minutes a mixture of 0.16 ml (0.16 gram, 2.7 mmole) ethanolamine, 0.34 ml (0.25 gram, 2.4 mmole) triethylamine and 50 ml THF. After all the solution was added, the resulting solution was stirred for an additional 20 minutes and then removed from the ice bath and stirred overnight at room temperature.

The solution was filtered using filter paper (Whatman #2). The residue remaining on the filter paper was dried under reduced pressure to yield 1.2 gram of an off-white residue.

The 1.2 gram off-white residue was dissolved in a mixture of 24 ml glacial acetic acid and 10 ml water, maintained at 70° C. for 1 hour and allowed to cool to room temperature. The product was extracted from the acetic acid solution by twice washing with 50 ml of a 2:1 chloroform:methanol extraction solution. The solvents of the extraction solution were evaporated leaving 0.94 gram (1.7 mmol) rac-1-hexadecyl-2-(5'-hexenyl)-3-phosphoethanolamine, a yield of 85% relative to the rac-1-Hexadecyl-2-(5'-hexenyl)-glycerol.

Preparation of rac-1-hexadecyl-2-(5'-hexenyl)-3-phosphocholine from rac-1-hexadecyl-2-(5% hexenyl)-3-phosphoethanolamine rac-1-hexadecyl-2-(5'-hexenyl)-3-phosphocholine was prepared in accordance with the teachings of the present invention, as is described in scheme XIV below.

Scheme XIV

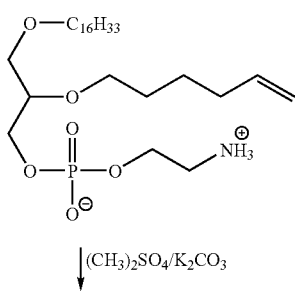

-continued

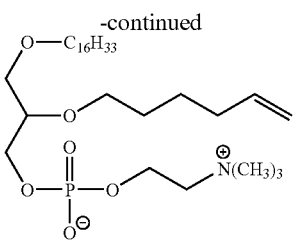

To a three-necked flask equipped with a magnetic stirrer 0.50 gram (0.99 mmole) rac-1-hexadecyl-2-(5'-hexenyl)-3-phosphoethanolamine, 50 ml isopropanol and 18 ml $CH_2Cl_2$ are added. While stirring, a mixture of 5 gram $K_2CO_3$ and 10 ml water was added and the temperature of the solution was maintained at between about 35° C. and about 40° C. while a mixture of 1.0 ml (1.3 gram, 11 mmole) dimethylsulfate and 10 ml isopropanol was added dropwise over a period of 45 minutes. After all the solution was added, the solution was stirred for an additional 90 minutes. The solution was allowed to cool to room temperature. The resulting product was extracted from the solution by thrice washing with 50 ml of a 2:1 chloroform:methanol solution. The solvents of the solution were evaporated leaving 0.50 gram (0.82 mmole) rac-1-hexadecyl-2-(5'-hexenyl)-3-phosphocholine, a yield of 92% yield relative to rac-1-hexadecyl-2-(5'-hexenyl)-3-phosphoethanolamine.

Purity was confirmed with thin-layer chromatography on alumina using an elution solvent of chloroform:methanol:water (70:26:4). The identity of the rac-1-hexadecyl-2-(5'-hexenyl)-3-phosphocholine was confirmed using $^{13}C$-NMR.

Example 5

Preparation of 1-Hexadecyl-2-(4'-carboxymethyl)butyl-3-phosphocholine

A solution of 1-Hexadecyl-2-(5'-carboxymethyl)butyl-glycerol (0.86 grams), 0.34 gram (2.6 mmole) triethylamine and 50 ml tetrahydrofuran was added dropwise, over 25 minutes to an ice-cooled solution of 0.24 ml (0.39 gram, 2.6 mmole) $POCl_3$ and 10 ml tetrahydrofuran (THF). The resulting mixture was stirred for additional 10 minutes in an ice-bath and for 45 minutes at room temperature (23° C.). The reaction mixture was then cooled in an ice-bath and a solution of ethanolamine (0.16 ml) and triethylamine (0.64 ml) in THF (50 ml) was added dropwise thereto under vigorous stirring. The stirring was continued for additional 10 minutes in an ice-bath and further continued at room temperature for overnight. The reaction mixture was then filtered and the solvent removed under reduced pressure. The residue was dissolved in a mixture of acetic acid (24 ml) and water (10 ml) and the solution was heated to 70° C. for 1 hour. After cooling to room temperature, the mixture was extracted with chloroform (2×25 ml) and the solvent was removed under reduced pressure. The residue was dissolved in a mixture of iso-propanol (50 ml) and dichloromethane (18 ml). Potassium carbonate (5.0 gram) in water (10 ml) was added thereto and the resulting mixture was warmed to 35-40° C. A solution of dimethylsulfate (1 ml) in 10 ml iso-propanol was then added dropwise over 45 minutes. After additional 90 minutes the mixture was extracted with chloroform (3×50 ml) and the solvent was removed under reduced pressure to give 1.10 grams of 1-Hexadecyl-2-(4'-carboxymethyl)butyl-3-phosphocholine (92% yield).

Preparation of 1-Hexadecyl-2-(4'-carboxy)butyl-3-phosphocholine: 1-Hexadecyl-2-(4'-carboxymethyl)butyl-3-phosphocholine was dissolved in methanol (25 ml). Sodium hydroxide (1.0 gram) dissolved in 90% methanol (20 ml) was added to the methanolic solution and the reaction mixture was stirred at room temperature for 5 hours. The pH of the reaction was adjusted to 4 by adding sodium dihydrogen phosphate. Water (50 ml) and chloroform (50 ml) were added, the organic phase was collected and the solvent was removed under reduced pressure. The residue was dissolved in chloroform, dried over anhydrous $Na_2SO_4$, filtered and the solvent was removed under reduced pressure. 1-Hexadecyl-2-(4'-carboxy)butyl-3-phosphocholine (0.71 grams) were obtained (66% yield).

Example 6

Preparation of 1-hexadecyl-2-(4'-carboxy)butyl-3-phosphocholine (CI-201) via direct oxidation of an unsaturated bond (a scalable process)

A process of preparing 1-hexadecyl-2-(4'-carboxy)butyl-3-phosphocholine (CI-201), which can be readily scaled-up for industrial manufacturing of the product is depicted in Scheme XV below:

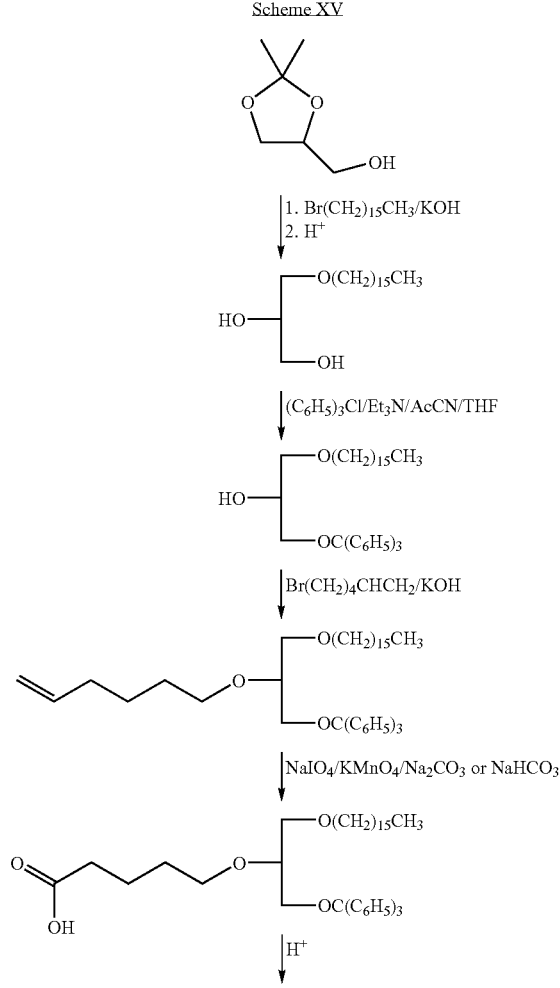

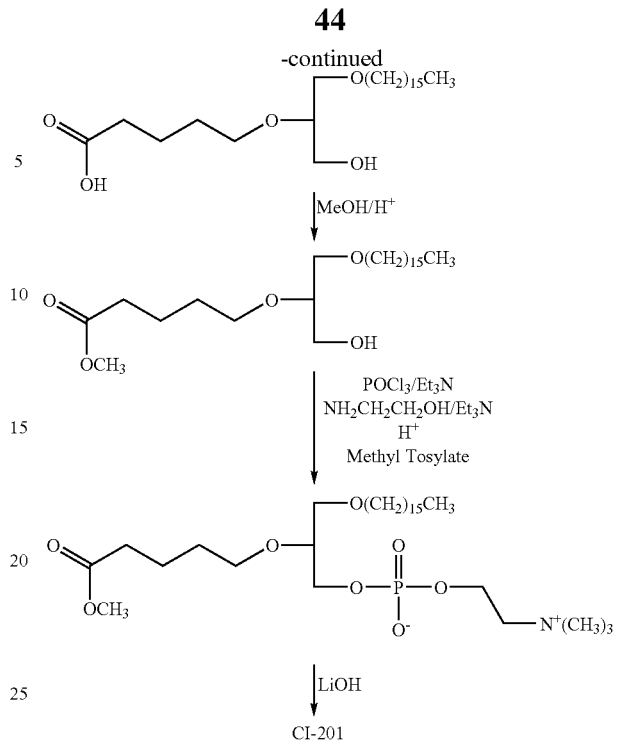

In this process, 1-hexadecyl-2-(5'-hexenyl)-3-tritylglycerol is directly oxidized to obtain the corresponding carboxylic acid in a one-step procedure, thus circumventing the need to perform the oxidation via a multiple-step procedure that requires laborious separations of the intermediates. The oxidation step is performed using safe, efficient and less hazardous oxidizing agents. Purification procedures of all the intermediates are performed while avoiding the use of industrially inapplicable column chromatography.

This process was efficiently scaled-up, so as to industrially manufacture CI-201.

Preparation of 1-Hexadecyl-glycerol: (R)-(−)-2,2-dimethyl-1,3-dioxolane-4-methanol (11 grams), powdered potassium hydroxide (20 grams) and hexadecyl bromide (27.96 grams) in toluene (150 ml) were stirred and refluxed for 6 hours, while removing the water formed by azeotropic distillation. The volume of the solvent was gradually reduced to about 40 ml. The reaction mixture was cooled to room temperature; water was added (100 ml) and the resulting mixture was extracted with dichloromethane (3×75 ml). The combined organic phase was washed with water (50 ml) and the solvent removed under reduced pressure. The residue was dissolved in 200 ml mixture of 90:10:5 methanol:water:concentrated hydrochloric acid (v/v) and the resulting solution was refluxed for 2 hours, followed by cooling to room temperature and addition of water (100 ml). The product was extracted with dichloromethane (3×100 ml), and the organic phase was washed consecutively with water (100 ml), saturated aqueous solution of sodium carbonate (100 ml) and again with water (100 ml). The solvent was removed under reduced pressure and the product was crystallized from hexane (200 ml) to give 21.69 grams (yield 82%) of pure 1-hexadecyl-glycerol, upon drying in a desiccator under reduced pressure.

Preparation of 1-Hexadecyl-3-trityl-glycerol: 1-Hexadecyloxy-glycerol (20 grams) and triphenylchloromethane (21.29 grams) were placed in dry THF (369 ml) and dry acetonitrile (93 ml). Triethylamine (17.75 ml) was added and the reaction mixture was refluxed for 17 hours. The reaction mixture was thereafter cooled to room temperature, poured on ice (100 grams), transferred to a separatory funnel and extracted with ether. The organic phase was washed consecutively with water (200 ml), diluted (1.5%) $H_2SO_4$ (2×200 ml), water (200 ml), saturated aqueous sodium bicarbonate (200 ml) and again with water (200 ml), dried over anhydrous sodium sulfate and the solvent removed under reduced pressure to give 36.86 grams of crude product.

The residue was dissolved in hot hexane (200 ml) and the resulting solution was cooled at 4° C. overnight. The resulting precipitate was filtered to yield 23.77 grams of the purified compound. Additional purified product was collected by removing the solvent from the mother liquor under reduced pressure and dissolving the residue again in hot hexane (50 ml). The resulting solution was cooled at 4° C. overnight and the precipitate filtered to afford additional 6.94 grams of the product and a total amount of 30.71 grams.

Preparation of 1-Hexadecyl-2-(5'-hexenyl)-3-tritylglycerol: 1-Hexadecyl-3-tritylglycerol (19.94 grams), 6-bromo-1-hexene (6.98 grams, 5.73 ml) and powdered potassium hydroxide (15 grams) in hexane (350 ml) were stirred and refluxed for 8 hours, while removing the water formed by azeotropic distillation. The reaction mixture was then cooled to room temperature, transferred to a separatory funnel and washed with water (2×200 ml). The solvent was thereafter removed under reduced pressure and the residue was dissolved in hexane (150 ml) and washed again with water (2×200 ml). The organic solution was kept at 4° C. overnight, during which precipitation of byproducts occurred. Filtration and removal of the solvent under reduced pressure gave 19.86 grams (86.6% yield) of 1-hexadecyl-2-(5'-hexenyl)-3-tritylglycerol.

Preparation of 1-hexadecyl-2-(4'-carboxy)butyl-sn-glycerol: In a three-neck round bottom flask equipped with thermometer and dropping funnel, sodium periodate (150.16 grams, 702 mmol, 9 equivalents) were suspended in 500 ml water. After addition of sodium bicarbonate (7.21 grams, 85.8 mmol, 1.1 equivalents) and potassium permanganate (2.47 grams, 15.6 mmol, 0.2 equivalent), the suspension was heated to 40° C. 1-Hexadecyl-2-(5'-hexenyl)-3-tritylglycerol (50.00 grams, 78.0 mmol) was dissolved in tert-butanol (500 ml) and the solution was added to the $NaIO_4/KMnO_4$ mixture during 1 hour. After 1.5 hours, analysis by TLC showed 80% conversion. Additional amount of potassium permanganate (0.62 gram, 3.9 mmol, 0.05 equivalent) was added and the mixture was stirred for 1.5 hours. Analysis by TLC showed less than 5% of the starting material. The reaction mixture was then cooled to room temperature and transferred to separation funnel.

The intermediate 1-Hexadecyl-2-(4'-carboxy)butyl-3-tritylglycerol was extracted with hexane (200 ml). The organic phase was washed with a solution of $Na_2S_2O_5$ (15 grams) in 100 ml water. Diluted hydrochloric acid (0.65 ml concentrated HCl in 13 ml water) was added to the organic phase and 200 ml of the solvent were distilled under reduced pressure. The remaining clear solution was heated to 80° C. for 6 hours. Analysis by TLC showed less than 5% of intermediate 1-Hexadecyl-2-(4'-carboxy)butyl-3-tritylglycerol. Additional volume of 250 ml solvent was distilled off.

The residue was treated with 100 ml water and 10 ml 30% NaOH to reach pH=12. The precipitated triphenylmethanol was filter off and washed 4 times with 10 ml water. The filtrate was extracted with a mixture of 50 ml hexane and 50 ml ethyl acetate to remove remaining triphenylmethanol and other impurities. The sodium salt of 1-hexadecyl-2-(4'-carboxy)butyl-sn-glycerol, present in the aqueous phase, was protonated with concentrated hydrochloric acid (8.45 ml, 101.4 mmol, 1.3 equivalents, pH=1). The resulting free carboxylic acid was extracted with hexane (100 ml). Evaporation to dryness and co-evaporation with 100 ml hexane gave 27.00 grams of crude 1-hexadecyl-2-(4'-carboxy)butyl-sn-glycerol.

The crude product was crystallized by dissolving in a mixture of acetone and hexane (7 ml/68 ml) and cooling to 0° C. The precipitate was filtered and washed with cold hexane (2×7 ml) and dried. 1-Hexadecyl-2-(4'-carboxy)butyl-sn-glycerol was obtained as an off-white solid (20.90 grams, 50.2 mmol, 64.3% yield).

Preparation of 1-Hexadecyl-2-(4'-carboxymethyl)butyl-sn-glycerol: 1-Hexadecyl-2-(4'-carboxy)butyl-sn-glycerol (15.0 grams, 36.0 mmol) was dissolved in methanol (100 ml) and concentrated hydrochloric acid (3 ml) was added. The reaction mixture was stirred at room temperature overnight. Triethylamine was thereafter added until the reaction mixture reaches pH=7. The solution was transferred to separatory funnel and extracted with hexane (2×200 ml). The organic phase was washed with water and evaporation to dryness and co-evaporation with 100 ml hexane gave 14.92 grams of 1-hexadecyl-2-(4'-carboxymethyl)butyl-sn-glycerol (34.65 mmol, 96.2% yield).

1-Hexadecyl-2-(4'-carboxymethyl)butyl-sn-glycero-3-phosphocholine: A solution of 1-Hexadecyl-2-(4'-carboxymethyl)butyl-glycerol (8.60 grams, 19.97 mmol), and triethylamine (2.63 grams, 3.62 ml, 26 mmol) in 500 ml THF was added dropwise, over 25 minutes, to an ice-cooled solution of $POCl_3$ (3.90 grams, 2.40 ml, 26 mmol) in 100 ml THF. The resulting mixture was stirred for an additional 10 minutes in an ice-bath and for 45 minutes at room temperature (23° C.). A solution of ethanolamine (1.6 ml) and triethylamine (6.4 ml) in THF (500 ml) was then added dropwise under vigorous stirring to an ice-cooled reaction mixture. The stirring was continued for an additional 10 minutes in an ice-bath and further continued at room temperature for overnight. The reaction mixture was thereafter filtered and the solvent removed under reduced pressure. The residue was dissolved in a mixture of acetic acid (24 ml) and water (100 ml) and heated to 70° C. for 1 hour. The reaction mixture was thereafter cooled to room temperature and extracted with dichloromethane (2×250 ml). The solvent was removed under reduced pressure, to afford crude 1-hexadecyl-2-(4'-carboxymethyl)butyl-sn-glycero-3-phosphoethanolamine.

The crude 1-hexadecyl-2-(4'-carboxymethyl)butyl-sn-glycero-3-phosphoethanolamine was dissolved in a mixture of isopropanol (500 ml) and dichloromethane (180 ml). A solution of potassium carbonate (50 grams) in water (100 ml) was added to reach a pH above 11, and the solution was kept at 35-40° C. during the dropwise addition of methyltosylate (11.15 grams) in 100 ml of iso-propanol in a time period of 45 minutes. After additional 90 minutes, the mixture was acidified with hydrochloric acid. Water (100 ml) and dichloromethane (550 ml) were added and the phases separated. The organic phase was washed with water (100 ml) and the solvent removed under reduced pressure to give 11.0 grams of 1-hexadecyl-2-(5'-carboxymethyl)butyl-3-phosphocholine (18.46 mmol, 92.45% yield).

Preparation of 1-Hexadecyl-2-(4'-carboxy)butyl-3-phosphocholine: 1-Hexadecyl-2-(4'-carboxymethyl)butyl-3-phosphocholine was dissolved in isopropanol (250 ml). Lithium hydroxide monohydrate (1.68 grams) was added and the reaction mixture was stirred at room temperature overnight. Isopropanol was partially evaporated by distillation and the pH of the reaction was brought acidic by addition of hydrochloric acid. Water (250 ml) was added and the solution extracted with dichloromethane (2×250 ml). The solvent was thereafter removed under reduced pressure and co-evaporated with dichloromethane to give crude 1-hexadecyl-2-(5'-carboxy)butyl-3-phosphocholine.

The crude 1-hexadecyl-2-(4'-carboxy)butyl-3-phosphocholine was purified by chromatography on a silica gel column. Dichloromethane followed by a mixture of dichloromethane, methanol, water, and triethylamine was used to elute the product from the column. The fractions containing the product were combined and evaporated. The resulting product was dried under vacuum. 7.10 grams of pure 1-hexadecyl-2-(4'-carboxy)butyl-3-phosphocholine (12.2 mmol, 66.1% yield) were obtained.

Example 7

Preparation of 1-hexadecyl-2-(6'-carboxy)hexanyl-sn-glycero-3-phosphocholine direct introduction of oxidized moiety—Route II Preparation of 1-hexadecyl-2-(6'-carboxyethyl)hexanyl-3-trityl-sn-glycerol:

slowly. The reaction mixture was stirred and refluxed for 4 hours and was thereafter cooled to room temperature, poured on ice and extracted with diethyl ether (3×100 ml). The organic phase was washed with water (100 ml), saturated aqueous sodium bicarbonate solution (100 ml) and water (100 ml). After drying over anhydrous sodium sulfate and filtration, the solvent was removed under reduced pressure. N-hexane was added and the mixture kept at 4° C. overnight. After filtration of the precipitate, the filtrate was concentrated by evaporation and the yellow solution was kept at 4° C. overnight. After filtration of the precipitate the yellow solution was warmed to room temperature and the solvent removed under reduced pressure to give 3.1 grams yellow oil. The residue was purified by chromatography on silica gel column (140 grams). The elution started with 300 ml chloroform, the polarity increased to 300 ml CHCl$_3$: EtOAc 90%: 10% then to 300 ml CHCl$_3$: EtOAc 80%:20% and 300 ml CHCl$_3$: EtOAc 70%:30% and finally to 300 ml CHCl$_3$: EtOAc 60%:40%. The product was collected from fractions eluted by the latter two eluent mixtures, upon combining the Scheme XVI

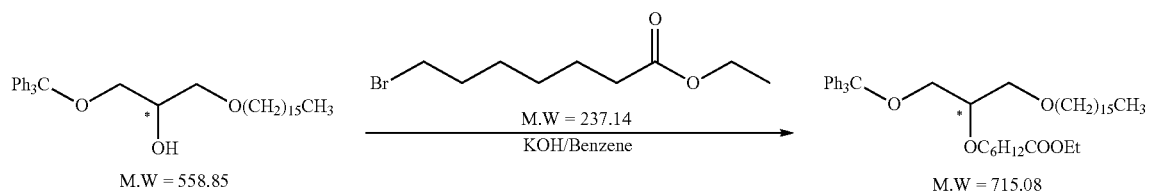

To a solution of 1-hexadecyl-3-trityl-sn-glycerol (5.0 grams, 8.95 mmol), and ethyl 7-bromo-heptanoate (2 ml, 2.44 grams, 10.29 mmol) in benzene (70 ml), powdered KOH (23 grams) was added. The reaction mixture was stirred and refluxed for 14 hours, while removing the water formed by azeotropic distillation. The reaction mixture was cooled to room temperature, washed with water (3×70 ml) and dried over anhydrous sodium sulfate. The solvent was removed under reduced pressure and the residue was dissolved in hexane (25 ml) and cooled to 4° C. The byproduct precipitated and was filtered off. The solvent was removed from the filtrate under reduced pressure to give 5 grams of 1-hexadecyl-2-(6'-carboxyethyl)hexanyl-3-trityl-sn-glycerol as a white solid (6.99 mmol, 78.1% yield).

Preparation of 1-hexadecyl-2-(6'-carboxyethyl)hexanyl-sn-glycerol:

Scheme XVII

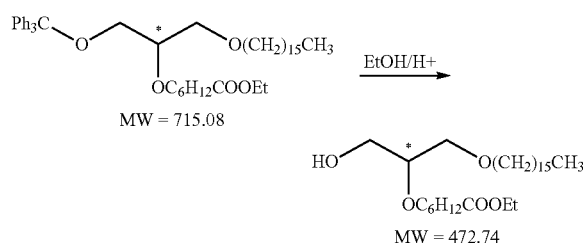

To a solution of 1-hexadecyl-2-(6'-carboxyethyl)hexanyl-3-trityl-sn-glycerol (5.0 grams, 7 mmol) in ethanol (90 ml), concentrated hydrochloric acid (32%, 20 ml) was added fractions and removing the solvent under reduced pressure. 1.34 grams of colorless oil were obtained, and dried under reduced pressure with phosphorus pentoxide to give 1-hexadecyl-2-(6'-carboxyethyl)hexanyl-sn-glycerol as a colorless solid (2.83 mmol, 40.5% yield).

Preparation of 1-hexadecyl-2-(6'-carboxyethyl)hexanyl-sn-glycero-3-phosphoethanolamine:

Scheme XVIII

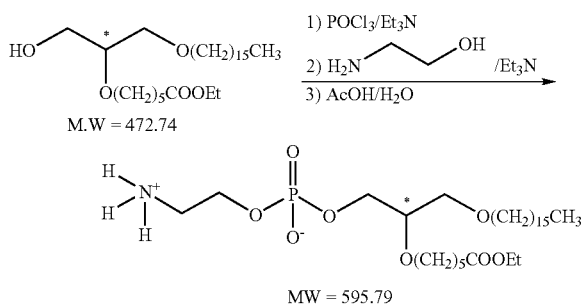

1-Hexadecyl-2-(6'-carboxyethyl)hexanyl-sn-glycerol (1.34 gram, 2.83 mmol) and triethylamine (1.2 ml) were dissolved in 15 ml THF. The solution was added dropwise for over 15 minutes to an ice-cooled solution of POCl$_3$ (0.8 ml, 8.5 mmol) in 10 ml THF. The stirring was continued for additional 10 minutes with cooling and further continued for 45 minutes at room temperature. A solution of ethanolamine (0.52 ml, 8.5 mmol) and triethylamine (2.4 ml) in THF (25 ml) was added dropwise over 15 minutes to the ice-cooled reaction mixture. The stirring was continued for 10 minutes, the cooling bath was thereafter removed and the reaction mixture was stirred at room temperature overnight. The reaction mixture was then filtered and the solvent removed under reduced pressure. The residue was dissolved in a mixture of acetic acid (24 ml) and water (10 ml) and heated to 70° C. for 1 hour. The mixture was thereafter extracted with chloroform (3×50 ml), the organic phase washed with water (2×50 ml) and the solvent removed under reduced pressure to give 1.87 grams of crude 1-hexadecyl-2-(6'-carboxyethyl)hexanyl-sn-glycero-3-phosphoethanolamine as yellow oil.

Preparation of 1-hexadecyl-2-(6'-carboxyethyl)hexanyl-sn-glycero-3-phosphocholine:

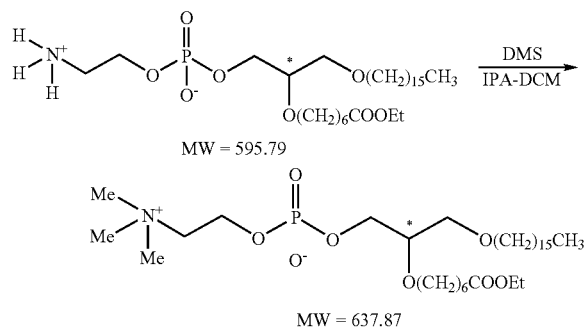

1-hexadecyl-2-(6'-carboxyethyl)hexanyl-sn-glycero-3-phosphoethanolamine was dissolved in mixture of isopropanol (50 ml) and dichloromethane (18 ml). A solution of potassium carbonate (2.17 grams) in water (10 ml) was added dropwise over 5 minutes while keeping the solution at 35-40° C. Dimethylsulfate (1.52 ml, 15.69 mmol) in isopropanol (10 ml) was added dropwise at 40° C. during 10 minutes and the reaction was stirred at 40° C. for 90 minutes. Water was then added and the mixture was extracted with chloroform (2×50 ml). The organic phase was washed with water (50 ml) and the solvent was removed under reduced pressure to give 1.8 grams of 1-hexadecyl-2-(6'-carboxyethyl)hexanyl-sn-glycero-3-phosphocholine as wax.

Preparation of 1-hexadecyl-2-(6'-carboxy)hexanyl-sn-glycero-3-phosphocholine:

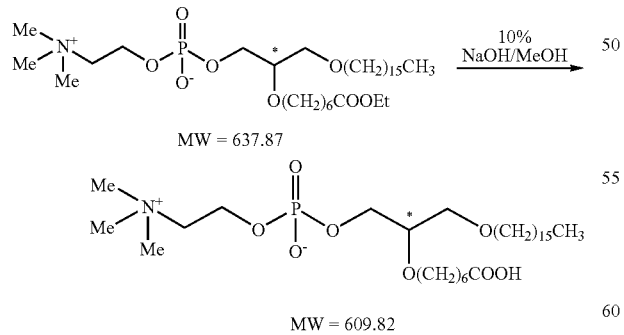

To mixture of 1-hexadecyl-2-(6'-carboxyethyl)hexanyl-sn-glycero-3-phosphocholine (1.8 grams, 2.82 mmol) in methanol (50 ml), a solution of 10% sodium hydroxide was added. The mixture was stirred at room temperature for 5 hours. The pH of the reaction was adjusted to 4-5 by adding sodium dihydrogen phosphate, and water (70 ml) and chloroform (70 ml) were added. The phases were separated and the solvent was removed under reduced pressure. The residue was dissolved in chloroform, dried over anhydrous sodium sulfate, filtered and the solvent removed under reduced pressure to give 1.29 grams of the crude product as a white wax.

The crude product was purified by chromatography on silica gel column (62 grams). The elution started with 200 ml CHCl$_3$:MeOH 80%:20% to elute the non polar residues, then the polarity increased to 200 ml CHCl$_3$:MeOH:Water 70%:26%: 4% and finally to 300 ml CHCl$_3$:MeOH:Water 60%:35%:5%. The product was eluted with the final mixture. The fractions were collected, the solvent was removed under reduced pressure, the residue was dissolved in chloroform and dried over anhydrous sodium sulfate and the solvent was removed reduced pressure. The product was dried under reduced pressure with phosphorus pentoxide. 1.0 gram of 1-hexadecyl-2-(6'-carboxy)hexanyl-sn-glycero-3-phosphocholine as white wax was obtained (58.1% yield).

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of preparing a compound having a glycerolic backbone and at least one oxidized moiety-containing residue attached to the glycerolic backbone via an ether bond, the compound having the general Formula II:

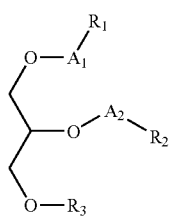

Formula II wherein:

$A_1$ is selected from the group consisting of $CH_2$, $CH=CH$ and $C=O$;

$A_2$ is $C_2$:, $R_1$ is an alkyl having 1-30 carbon atoms;

$R_2$ is

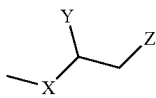

whereas:
X is an alkyl chain having 1-24 carbon atoms;
Y is hydrogen; and
Z is

Formula I

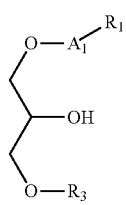

$R_3$ is selected from the group consisting of hydrogen, alkyl, aryl, phosphoric acid, phosphoryl choline, phosphoryl ethanolamine, phosphoryl serine, phosphatidyl choline, phosphatidyl ethanolamine, phosphatidyl serine, phosphatidyl cardiolipin, phosphatidyl inositol, phosphoryl cardiolipin, phosphoryl inositol, ethylphosphocholine, phosphorylmethanol, phosphorylethanol, phosphorylpropanol, phosphorylbutanol, pho sphorylethanolamine-N-lacto se, phosphoethanolamine-N-[methoxy (propylene glycol)], phosphoinositol-4-phosphate, phosphoinosito1-4,5-biphosphonate, pyrophosphate, pho sphoethanolamine-diethylenetriamine-pentaacetate, dinitrophenyl-phosphoethanolamine, and phosphoglycerol,
the method comprising:
providing a first compound having a glycerolic backbone and at least one free hydroxyl group, said first compound having the general formula I:

Formula I

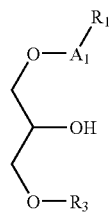

wherein:
$A_1$ is absent or is selected from the group consisting of $CH_2$, CH=CH and C=O:
$R_1$ is selected from the group consisting of H and a hydrocarbon chain having from 1 to 30 carbon atoms; and
$R_3$ is selected from the group consisting of hydrogen, alkyl, aryl, phosphoric acid, phosphoryl choline, phosphoryl ethanolamine, phosphoryl serine, phosphatidyl choline, phosphatidyl ethanolamine, phosphatidyl serine, phosphatidyl cardiolipin, phosphatidyl inositol, phosphoryl cardiolipin, phosphoryl inositol, ethylphosphocholine, phosphorylmethanol, phosphorylethanol, phosphorylpropanol, phosphorylbutanol, pho sphorylethanolamine-N-lacto se, phosphoethanolamine-N-[methoxy (propylene glycol)], phosphoinositol-4-phosphate, phosphoinosito1-4,5-biphosphonate, pyrophosphate, phosphoethanolamine-diethylenetriamine -pentaacetate, dinitrophenyl-phosphoethanolamine, and phosphoglycerol;
providing a compound having at least one oxidized moiety and at least one reactive group, said oxidized moiety being a carboxylic ester;
reacting said first compound and said compound having at least one oxidized moiety and at least one reactive group in the presence of an inorganic base, to thereby obtain a reaction mixture containing a compound having a glycerolic backbone and at least one carboxylic ester-containing residue attached to the glycerolic backbone via an ether bond,
wherein when said compound having said at least one oxidized moiety and dais at least one reactive group is 5 carbon atoms in length, said reacting in the presence of said inorganic base is performed under conditions which do not adversely affect reaction efficiency, and
wherein when $R_3$ of said compound is hydrogen, the method further comprises, prior to said reacting said first compound and said compound having said at least one oxidized moiety and said at least one reactive group, protecting a free hydroxyl group at position sn-3 of said glycerolic backbone with a protecting group;
hydrolyzing said carboxylic ester so as to produce said Z; and
isolating the compound having a glycerolic backbone and at least one oxidized moiety-containing residue attached to the glycerolic backbone via an ether bond.

2. The method of claim 1, wherein said inorganic base is selected from the group consisting of sodium hydride, lithium aluminum hydride, sodium amide, sodium hydroxide, potassium hydroxide and any mixture thereof.

3. The method of claim 1, wherein the compound having a glycerolic backbone and at least one oxidized moiety-containing residue attached to the glycerolic backbone further comprises a phosphorus-containing moiety attached to the glycerolic backbone, such that $R_3$ is selected from the group consisting of phosphoric acid, phosphoryl choline, phosphoryl ethanolamine, ephosphoryl serine, phosphatidyl choline, phosphatidyl ethanolamine, phosphatidyl serine, phosphatidyl cardiolipin, phosphatidyl inositol, phosphoryl cardiolipin, phosphoryl inositol, ethylphosphocholine, phosphorylmethanol, phosphorylethanol, phosphorylpropanol, phosphorylbutanol, phosphorylethanolamine-N-lactose, phosphoethanolamine-N-[methoxy(propylene glycol)], phosphoinositol-4-phosphate, phosphoinositol-4,5-biphosphonate, pyrophosphate, phosphoethanolamine-diethylenetriamine-pentaacetate, dinitrophenyl-phosphoethanolamine, and phosphoglycerol,
the method further comprising, prior to or subsequent to reacting said first compound and said compound having said at least one oxidized moiety and said at least one reactive group, or subsequent to isolating said compound having said at least one ester-containing residue attached to said glycerolic backbone:
reacting said first compound or said compound having said at least one ester-containing residue attached to said glycerolic backbone with a phosphorus-containing moiety, to thereby obtain said compound having a glycerolic backbone and at least one oxidized moiety-containing residue attached to the glycerolic backbone and further having a phosphorus-containing moiety attached to the glycerolic backbone.

4. The method of claim 3, wherein reacting said first compound or said compound having said at least one ester-containing residue attached to said glycerolic backbone with said phosphorus-containing moiety comprises:

providing said first compound or said compound having said at least one carboxylic ester-containing residue attached to said glycerolic backbone, and further having a free hydroxyl group;

reacting said first compound or said compound having said at least one ester-containing residue attached to said glycerolic backbone with a reactive phosphorus-containing compound having a second reactive group capable of reacting with said free hydroxyl group and a third reactive group, to thereby provide said first compound or said compound having said at least one ester-containing residue attached to said glycerolic backbone, having a reactive phosphorus-containing group attached thereto; and converting said reactive phosphorus-containin group to said phosphorus-containing moiety.

5. The method of claim 4, wherein said reactive phosphorus-containing compound is phosphorus oxychloride (POCl3).

6. A method of introducing a phosphate moiety into a compound having a glycerolic backbone and having an oxidized moiety-containing or a pre-oxidized moiety-containing residue attached thereto via an ether bond, the method comprising:

providing a compound having a glycerolic backbone and an oxidized moiety -or a pre-oxidized moiety-containing residue attached to said glycerolic backbone via an ether bond and at least one a free hydroxyl group;

reacting said compound with a phosphorus-containing compound which is $POCl_3$, to thereby provide a compound having an oxidized moiety- or a pre-oxidized moiety-containing residue and a reactive phosphorus-containing group; and converting said reactive phosphorus-containing group to said phosphate moiety, thereby introducing the phosphate moiety into the compound.

7. The method of claim 6, wherein said oxidized moiety is selected from the group consisting of carboxylic acid, ester, acyl halide, aldehyde, acetal, diol and ketal.

8. The method of claim 6, wherein said pre-oxidized moiety is an unsaturated moiety.

9. The method of claim 1, wherein said compound having said at least one oxidized moiety and said at least one reactive group is more than 5 carbon atoms in length.

10. The method of claim 9, wherein said compound having said at least one oxidized moiety and said at least one reactive group is ethyl 7-bromoheptanoate.

* * * * *

UNITED STATES PATENT AND TRADEMARK OFFICE
CERTIFICATE OF CORRECTION

PATENT NO. : 8,124,800 B2  
APPLICATION NO. : 12/861921  
DATED : February 28, 2012  
INVENTOR(S) : Halperin et al.

Page 1 of 1

It is certified that error appears in the above-identified patent and that said Letters Patent is hereby corrected as shown below:

| Location in text | Previously | As corrected |
|---|---|---|
| Column 50, line 65, | $A_2$ is $C_2$:, | $A_2$ is $CH_2$; |
| Column 51, lines 12-23 | Z is (Formula I structure) | Z is (corrected structure) ; and |
| Column 51, lines 32-33 | pho sphorylethanolamine-N-lacto se | phosphorylethanolamine-N-lactose |
| Column 51, line 36 | pho sphoethanolamine | phosphoethanolamine |
| Column 51, line 67 to Column 52, line 1 | pho sphorylethanolamine-N-lacto se | phosphorylethanolamine-N-lactose |
| Column 52, lines 4-5 | diethylenetriamine - pentaacetate | diethylenetriamine-pentaacetate |
| Column 52, line 18 | dais | said |
| Column 53, line 18 | phosphorus-containin | phosphorus-containing |
| Column 53, line 22 | POCl3 | $POCl_3$ |
| Column 54, line 2 | oxidized moiety  -or | oxidized moiety- or |

Signed and Sealed this  
Nineteenth Day of June, 2012

David J. Kappos  
*Director of the United States Patent and Trademark Office*